United States Patent
Chen et al.

(10) Patent No.: US 11,679,143 B2
(45) Date of Patent: *Jun. 20, 2023

(54) FGF21 VARIANT, FUSION PROTEIN AND APPLICATION THEREOF

(71) Applicant: SUNSHINE LAKE PHARMA CO., LTD., Guangdong (CN)

(72) Inventors: Chao Chen, Dongguan (CN); Shushan Lin, Dongguan (CN); Yu Li, Dongguan (CN); Xiaofeng Chen, Dongguan (CN); Wenjia Li, Dongguan (CN); Liang Liu, Dongguan (CN); Zheng Fu, Dongguan (CN)

(73) Assignee: SUNSHINE LAKE PHARMA CO., LTD., Dongguan (CN)

( * ) Notice: Subject to any disclaimer, the term of this patent is extended or adjusted under 35 U.S.C. 154(b) by 140 days.

This patent is subject to a terminal disclaimer.

(21) Appl. No.: 16/960,254

(22) PCT Filed: Jan. 29, 2019

(86) PCT No.: PCT/CN2019/073686
§ 371 (c)(1),
(2) Date: Jul. 6, 2020

(87) PCT Pub. No.: WO2019/154189
PCT Pub. Date: Aug. 15, 2019

(65) Prior Publication Data
US 2021/0196794 A1    Jul. 1, 2021

(30) Foreign Application Priority Data

Feb. 8, 2018 (CN) .......................... 201810129589.3

(51) Int. Cl.
| | | |
|---|---|---|
| A61K 38/18 | (2006.01) | |
| A61K 47/68 | (2017.01) | |
| A61P 3/04 | (2006.01) | |
| A61P 3/10 | (2006.01) | |
| A61K 38/26 | (2006.01) | |
| C07K 14/50 | (2006.01) | |
| C07K 14/605 | (2006.01) | |

(52) U.S. Cl.
CPC .......... *A61K 38/1825* (2013.01); *A61K 38/26* (2013.01); *A61K 47/6811* (2017.08); *A61P 3/04* (2018.01); *A61P 3/10* (2018.01); *C07K 14/50* (2013.01); *C07K 14/605* (2013.01); *C07K 2319/30* (2013.01)

(58) Field of Classification Search
CPC . A61K 38/1825; C07K 14/50; C07K 2319/30
See application file for complete search history.

(56) References Cited

U.S. PATENT DOCUMENTS

| | | |
|---|---|---|
| 7,452,966 B2 | 11/2008 | Glaesner et al. |
| 7,491,697 B2 | 2/2009 | Beals et al. |
| 7,576,190 B2 | 8/2009 | Glaesner et al. |
| 7,582,607 B2 | 9/2009 | Frye et al. |
| 8,034,770 B2 | 10/2011 | Belouski et al. |
| 8,273,854 B2 | 9/2012 | Glaesner et al. |
| 8,361,963 B2 | 1/2013 | Belouski et al. |
| 8,541,369 B2 | 9/2013 | Dickinson et al. |
| 8,557,769 B2 | 10/2013 | Coskun et al. |
| 8,883,726 B2 | 11/2014 | Dickinson et al. |
| 8,927,492 B2 | 1/2015 | Darling et al. |
| 9,266,935 B2 | 2/2016 | Boettcher et al. |
| 9,422,353 B2 | 8/2016 | Darling et al. |
| 9,458,214 B2 | 10/2016 | Boettcher et al. |
| 2013/0252884 A1 | 9/2013 | Garibay et al. |
| 2014/0056893 A1 | 2/2014 | Coskun et al. |
| 2014/0073563 A1 | 3/2014 | Boscheinen et al. |
| 2014/0142023 A1 | 5/2014 | Sommerfeld et al. |
| 2014/0213512 A1 | 7/2014 | Ellison et al. |
| 2015/0231210 A1 | 8/2015 | Sommerfeld et al. |
| 2016/0194371 A1 | 7/2016 | Boscheinen et al. |
| 2018/0280474 A1 | 10/2018 | Xu et al. |
| 2018/0371041 A1 | 12/2018 | Sommerfeld et al. |
| 2019/0085043 A1 | 3/2019 | Boscheinen et al. |
| 2020/0024318 A1 | 1/2020 | Kim et al. |

FOREIGN PATENT DOCUMENTS

| | | |
|---|---|---|
| CN | 102558358 A | 7/2012 |
| WO | WO 2010/065439 * | 6/2010 |
| WO | 2010/129600 * | 11/2010 |
| WO | 2014/037373 * | 3/2014 |
| WO | 2016/114633 A1 | 7/2016 |
| WO | 2018/166461 A1 | 9/2018 |

OTHER PUBLICATIONS

Apr. 19, 2019 Search Report issued in International Patent Application No. PCT/CN2019/073686.
Apr. 19, 2019 Written Opinion of the International Searching Authority issued in International Patent Application No. PCT/CN2019/073686.

* cited by examiner

*Primary Examiner* — Gyan Chandra
(74) *Attorney, Agent, or Firm* — Oliff PLC

(57) ABSTRACT

A fibroblast growth factor 21 (FGF21) variant, further to a FGF21 variant fusion protein, a protein multimer, and use thereof can significantly improve the binding ability with the target and can be used to treat metabolic diseases.

19 Claims, 7 Drawing Sheets

Specification includes a Sequence Listing.

FGF21 VARIANT, FUSION PROTEIN AND APPLICATION THEREOF

CROSS REFERENCE TO RELATED APPLICATION

This application claims priority to Chinese Patent Application Serial No. 201810129589.3, filed on Feb. 8, 2018, which is hereby incorporated by reference in its entirety. The present application contains a Sequence Listing that has been submitted electronically in ASCII format and is hereby incorporated by reference in its entirety. The ASCII copy, created on Jan. 8, 2021, is named Substitute Sequence Listing_ST25.txt and is 77,824 bytes in size.

FIELD OF THE INVENTION

The present invention relates to a fibroblast growth factor 21 (FGF21) variant, a fusion protein and/or a protein multimer thereof, which can be used for the treatment of metabolic diseases.

BACKGROUND OF THE INVENTION

At present, there are three categories of drugs for the treatment of diabetes: oral small molecule drugs, insulin and GLP-1 receptor agonist drugs. Long-term treatment of small molecule drugs leads to obvious side effects, and post-diabetic glycemic control is not satisfactory. Treatment of diabetes with insulin requires multiple injections (at least once daily), and hypoglycemia is easily triggered by differences in individual dosages. A single GLP-1 receptor agonist is not a first-line agent and has limited efficacy in cardiovascular complications caused by abnormal metabolism of diabetes.

Glucagon-like peptide-1 (GLP-1) is a type of incretin secreted by intestinal L cells. It stimulates islet β-cells to secrete insulin, maintaining insulin balance in patients. Natural GLP-1 survives only up to 2 minutes in vitro and therefore is not suitable as a drug. For a few years now, several parties including Eli Lilly, Novo Nordisk, GSK have been competitively seeking to transform the protein in order to obtain a long-acting GLP-1 class of hypoglycemic drugs. Type II diabetes has two major hallmarks: peripheral insulin resistance and impaired glucose-dependent insulin secretion of pancreatic beta cells. Metabolic disorders are often caused by a variety of complex factors, so the treatment of multiple metabolic pathways is considered much more potential.

FGF21 belongs to one of the members of FGF (fibroblast growth factors, FGFs) family. Since the discovery of the first FGF (FGF1 or aFGF) in 1976, 22 members of the family have been found in the human body. The biological functions of FGFs are very diverse. So far, studies have found that FGFs are involved in the regulation of a series of physiological activities including cell differentiation, proliferation and metabolism. The FGF21 gene was first cloned by Nishimura et al. It was not until 2005 that the biological activity of FGF21 was first revealed as a new metabolic regulator. Its follow-up studies found that FGF21 is involved in important metabolic regulation as a factor secreted by the liver.

In recent years, it has been found that FGF21 has a very good function of glycemic regulation. FGF21 can promote the absorption of glucose by fat cells and enhance insulin sensitivity. At the same time, compared with insulin, FGF21 does not cause side effects such as hypoglycemia, and can effectively protect β islet cells and promote regeneration and repair of islet β cells. Moreover, it does not lead to potential tumor risk because of its lack of mitotic activity, which makes FGF21 having a great potential for the promising treatment of type II diabetes as non-insulin drugs. In another aspect, unlike GLP hypoglycemic drugs, which are indirectly mediated by insulin, FGF21 itself can also stimulate GLUT1 receptors and promote the transport of glucose into cells. Therefore, FGF21 itself has the potential to be a drug for the treatment of type I diabetes.

In addition to targeting on diabetes, FGF21 also has a good lipid-lowering effect, which can improve lipid oxidation, regulate lipid decomposition and ketogenesis, thereby improving the body's lipid disorder. It is a potential lipid-lowering drug. Cardiovascular disease caused by weight gain and blood lipid is also an important complication of diabetic patients. FGF21 can well regulate body fat disorder while controlling blood sugar, and effectively prevent the occurrence of diabetic complications. It also has the potential to be a single lipid-lowering drug and a drug targeting on non-alcoholic fatty liver.

However, FGF21 also faces enormous challenges in drugability. In one aspect, FGF21 has a short half-life. Its half-life is only about one hour in a mouse model (Xu et al., 2009). The reason is that FGF21 is rapidly degraded by proteases in the body, and its tendency to form aggregates in vitro also leads to immunogenicity, which is not conducive to prolongation of half-life. In another aspect, FGF21 has limited biological activity in vivo, and its hypoglycemic ability and lipid-lowering ability are not strong enough to make it a usable drug alone. These factors make no anti-metabolic disease drug based on FGF21 available so far.

In order to enhance its biological activity in reducing blood sugar and lipid, it is necessary to modify FGF21 and enhance its interaction with target protein in order to enhance its effect in vivo. To date, no modification has been found that directly enhances the interaction of FGF21 with a target protein and directly enhances its biological activity in vivo.

SUMMARY OF THE INVENTION

In one aspect, the present invention provides a FGF21 variant. The amino acid sequence of the FGF21 variant includes one or more amino acid substitutions compared to the amino acid sequence of SEQ ID NO: 1, the one or more amino acid substitutions including an amino acid substitution at position 167.

In some embodiments, the amino acid substitution at position 167 is S167H.

In some embodiments, the one or more amino acid substitutions further comprise amino acid substitutions at one or more positions selected from the group consisting of position 98, position 171, position 175, position 113, position 114, and position 135.

In some embodiments, the one or more amino acid substitutions comprise an amino acid substitution of L98R.

In some embodiments, the one or more amino acid substitutions comprise an amino acid substitution of P171A or P171G.

In some embodiments, the one or more amino acid substitutions comprise an amino acid substitution R175L, R175P or R175H.

In some embodiments, the one or more amino acid substitutions comprise an amino acid substitution of G113R.

In some embodiments, the one or more amino acid substitutions comprise an amino acid substitution of L114Q.

In some embodiments, the one or more amino acid substitutions comprise an amino acid substitution of R135C.

In some embodiments, the one or more amino acid substitutions comprise amino acid substitutions selected from any one of the following combination of the amino acid positions: a) L98, 5167 and P171; b) L98, 5167, P171 and R175; and, c) L98, G113, L114, R135, 5167, P171 and R175.

In some embodiments, amino acid substitutions comprise the amino acid sequence of any one of SEQ ID NO: 3-4 and SEQ ID NO: 34-37.

In another aspect, the present invention provides a fusion protein comprising a FGF21 variant described herein.

In some embodiments, the fusion protein comprises an IgG constant region domain or a fragment thereof. In some embodiments, the IgG constant region domain or the fragment thereof comprises an IgG4 Fc domain. In some embodiments, the IgG4 Fc domain comprises the amino acid sequence of any one of SEQ ID NO: 5-6.

In some embodiments, the N-terminus of the FGF21 variant is directly or indirectly linked to the C-terminus of the IgG constant region domain or the fragment thereof. In some embodiments, the N-terminus of the FGF21 variant is linked to the C-terminus of the IgG constant region domain or the fragment thereof by a first linker. In some embodiments, the first linker comprises the amino acid sequence of any one of SEQ ID NO: 7-8.

In some embodiments, the fusion protein comprises the amino acid sequence of any one of SEQ ID NO: 9-14 and SEQ ID NO: 26-27.

In some embodiments, the fusion protein comprises GLP-1 receptor agonist portion. In some embodiments, the GLP-1 receptor agonist portion comprises GLP-1 analogues. In some embodiments, the GLP-1 receptor agonist portion comprises the amino acid sequence of any one of SEQ ID NO: 15 and SEQ ID NO: 28.

In some embodiments, the fusion protein comprises the IgG constant region domain or the fragment thereof and the GLP-1 receptor agonist portion, and the C-terminus of the GLP-1 receptor agonist portion is directly or indirectly linked to the N-terminus of the IgG constant region domain or the fragment thereof. In some embodiments, the C-terminus of the GLP-1 receptor agonist portion is linked to the N-terminus of the IgG constant region domain or the fragment thereof by a second linker. In some embodiments, the second linker comprises the amino acid sequence of any one of SEQ ID NO: 7-8.

In some embodiments, the second linker comprises the IgG constant region domain or the fragment thereof, the GLP-1 receptor agonist portion, and the FGF21 variant, and the N-terminus of the FGF21 variant is directly or indirectly linked to the C-terminus of the IgG constant region domain or the fragment thereof. In some embodiments, the C-terminus of the GLP-1 receptor agonist portion is linked to the N-terminus of the IgG constant region domain or the fragment thereof by a second linker, and the N-terminus of the FGF21 variant is linked to the C-terminus of the IgG constant region domain or the fragment thereof by a first linker. In some embodiments, the fusion protein comprises the amino acid sequence of any one of SEQ ID NO: 16-18.

In another aspect, the application provides a protein multimer comprising two or more fusion proteins described herein. In some embodiments, the protein multimer is a homodimer.

In another aspect, the application provides an isolated nucleic acid molecule encoding the FGF21 variant described herein or the fusion protein described herein.

In another aspect, provided herein is a vector comprising the isolated nucleic acid molecule.

In another aspect, provided herein is a cell comprising the vector.

In another aspect, provided herein is a method of preparing the FGF21 variant, the fusion protein, or the protein multimer. The method comprises culturing the cell described herein under conditions that permits expression and/or formation of the FGF21 variant, the fusion protein or the protein multimer.

In some embodiments, the method further comprises recovering the expressed and/or formed FGF21 variant, the fusion protein, or the protein multimer.

In another aspect, provided herein is a pharmaceutical composition comprising the FGF21 variant, the fusion protein or the protein multimer, and optionally one or more pharmaceutically acceptable carriers.

In another aspect, provided herein is use of the FGF21 variant, the fusion protein or the protein multimer in the manufacture of medicaments for treatment of metabolic diseases. In some embodiments, wherein the metabolic diseases are selected from diabetes, obesity and hepatic steatosis.

Other aspects and advantages of the present disclosure will be readily apparent to those skilled in the art from the following detailed description. Only the exemplary embodiments of the present disclosure are shown and described in the following detailed description. As will be recognized by those skilled in the art, the present disclosure will enable those skilled in the art to make modifications to the disclosed specific embodiments without departing from the spirit and scope of the invention. Accordingly, the drawings and the description of specification in the present application is merely illustrative, not restrictive.

DESCRIPTION OF THE DRAWINGS

Specific features of the invention in the present application are shown in the appended claims. The features and advantages of the invention in the application can be better understood by referring to the exemplary embodiments and drawings described in detail below. A brief description of the drawing is as follows:

EXAMPLES

Figure 1:
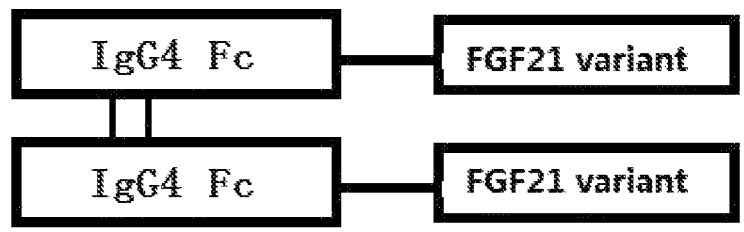
FIG. 1 shows a schematic diagram of a protein multimer of the present application in one embodiment.
Figure 2:
FIG. 2 shows a schematic diagram of a protein multimer of the present application in one embodiment.

Other features and advantages of the present application can be embodied in detailed description below. However, it should be understood that the embodiments of the present application is only given in an exemplary manner. It is obvious for those skilled in the art to make a variety of changes and improvements within the essence and scope of this application.

DEFINITION OF TERMINOLOGY

The human FGF21 wild-type sequence contains 209 amino acids with the NCBI reference sequence number NP_061986.1; a mature FGF21 sequence contains 181 amino acids, and lacks a leader sequence that the FGF21 wild-type contains. In the present application, the term "native FGF21 sequence" generally refers to the mature human FGF21 sequence having the amino acid sequence of SEQ ID NO: 1.

In the present application, the term "FGF21 variant" generally refers to a polypeptide containing an addition, deletion and/or substitution of one or more amino acid residues compared to the amino acid sequence of the native FGF21, and basically still having at least one nature of FGF21. The FGF21 variant can be modified at specific locations of natural FGF21 polypeptide by using natural or non-natural amino acids. The modifications includes insertion, replacement or deletion of one or more conservative or non-conservative amino acids at specific locations, as well as introduction of non-amino acid structures at specific positions. In the FGF21 variants described herein, the amino acid residues of the FGF21 variant are numbered in the sequence of SEQ ID NO: 1 as follows.

```
                                          (SEQ ID NO: 1)
HPIPDSSPLL QFGGQVRQRY LYTDDAQQTE AHLEIREDGT

VGGAADQSPE SLLQLKALKP GVIQILGVKT SRFLCQRPDG

ALYGSLHFDP EACSFRELLL EDGYNVYQSE AHGLPLHLPG

NKSPHRDPAP RGPARFLPLP GLPPALPEPP GILAPQPPDV

GSSDPLSMVG PSQGRSPSYA S
```

The FGF-21 variants described herein may also comprise deletion of amino acids, which may be N-terminal truncation, C-terminal truncation or internal deletion, or any combination thereof. These variants comprising N-terminal truncation, C-terminal truncation and/or internal deletion are referred to as "deletion variants" or "fragments" in the present application. The term "deletion variant" or "fragment" can be used interchangeably in the present application. The fragment may be naturally occurring (e.g., splice variants) or artificially constructed, e.g., through genetic means.

In the present application, the term "IgG constant region domain" generally refers to a polypeptide domain or a polypeptide fragment comprising an antibody heavy chain constant region, a hinge region and an antibody light chain constant region. The antibody may be an IgG antibody, for example, an antibody of the IgG1, IgG2, IgG3 or IgG4 subtype.

In the present application, the term "fragment" of an IgG constant region domain generally refers to a portion of an IgG constant region domain, but still retains at least a portion of its activity. For example, the fragment may include one or more domains or fragments of CL, CH1, hinge region, CH2 and CH3.

In the present application, the term "Fc domain" generally refers to a domain consisting of a hinge region of an antibody, CH2 and CH3 constant region portions. In the present application, the IgG4 Fc domain may comprise the amino acid sequence of SEQ ID NO: 5 or SEQ ID NO: 6.

In the present application, the term "GLP-1" generally refers to a biologically active GLP-1 (7-37) having the amino acid sequence of HAEGTFTSDV SSYLEGQAAK EFIAWLVKGR G. As used herein, "native GLP-1 sequence" refers to a native GLP-1 (7-37) sequence.

In the present application, the term "GLP-1 analogue" generally refers to an analog that retains the natural biological activity of GLP-1. For example, a GLP-1 analog described herein can comprise polypeptides obtained by introducing 1 to 10 (e.g., 1, 2, 3, 4, 5, 6, 7, 8, 9 or 10) amino acid substitutions (e.g., conservative amino acid substitutions), deletions or insertions into the natural GLP-1 sequence. The GLP-1 analog can extend the half-life of GLP-1 in vivo while retaining the natural biological activity of GLP-1. In some embodiments, the GLP-1 analog may comprise the amino acid sequence of

```
SEQ ID NO: 15 or SEQ ID NO: 28:
                                         (SEQ ID NO: 15)
HG⁸EGTFTSDVSSYLEE²²QAAKEFIAWLVKGG³⁶G (SEQ ID NO: 28)
HG⁸EGTFTSDVSSYLEE²²QAAKEFIAWLVKGRG.
```

In the present application, the term "biological activity of GLP-1" generally refers to a variety of biological effects induced by GLP-1, such as stimulating insulin secretion, inhibiting glucagon secretion, inhibiting gastric emptying, inhibiting gastric or intestinal motility and inducing weight loss. A striking feature of GLP-1 is that it can stimulate insulin secretion without risks associated with hypoglycemia.

In the present application, the term "conservative amino acid substitutions" may include residues of a native amino acid residue (i.e., a residue present at a given position in the wild-type FGF21 polypeptide sequence) replaced by a non-native residue (i.e., a residue not present at a given position in the wild-type FGF21 polypeptide sequence), so that there is little or no effect on the polarity or charge of amino acid residues at this position. Conservative amino acid substitutions also include non-naturally occurring amino acid residues that are commonly incorporated by chemical peptide synthesis rather than by a biological system synthesis. These include peptidomimetics and other reverse forms of amino acid portion.

The naturally occurring amino acid residues can be grouped into the following classes based on common side chain properties:
(1) Hydrophobic residues: norleucine, M, A, V, L, I;
(2) Neutral hydrophilic residues: C, S, T;
(3) Acid residues: D, E;
(4) Alkaline residues: N, Q, H, K, R;
(5) Residues affecting chain orientation: G, P; and
(6) Aromatic residues: W, Y, F.

Conservative substitutions may include one member of these categories being exchanged for another member of the same category.

Some conservative amino acid substitutions are shown in table 1:

TABLE 1

| Amino acid | Conservative amino acid substitutions |
|---|---|
| Ala | D-Ala, Gly, Aib, β-Ala, L-Cys, D-Cys |
| Arg | D-Arg, Lys, Orn, D-Orn |
| Asn | D-Asn, Asp, D-Asp, Glu, D-Glu, Gln, D-Gln |
| Asp | D-Asp, D-Asn, Asn, Glu, D-Glu, Gln, D-Gln |
| Cys | D-Cys, S-Me-Cys, Met, D-Met, Thr, D-Thr, L-Ser, D-Ser |
| Gln | D-Gln, Asn, D-Asn, Glu, D-Glu, Asp, D-Asp |
| Glu | D-Glu, Asp, D-Asp, Asn, D-Asn, Gln, D-Gln |
| Gly | Ala, D-Ala, Pro, D-Pro, Aib, β-Ala |
| Ile | D-Ile, Val, D-Val, Leu, D-Leu, Met, D-Met |
| Leu | D-Leu, Val, D-Val, Met, D-Met, Ile, D-Ile |
| Lys | D-Lys, Arg, D-Arg, Orn, D-Orn |
| Met | D-Met, S-Me-Cys, Ile, D-Ile, Leu, D-Leu, Val, D-Val |
| Phe | D-Phe, Tyr, D-Tyr, His, D-His, Trp, D-Trp |
| Pro | D-Pro |
| Ser | D-Ser, Thr, D-Thr, allo-Thr, L-Cys, D-Cys |
| Thr | D-Thr, Ser, D-Ser, allo-Thr, Met, D-Met, Val, D-Val |
| Tyr | D-Tyr, Phe, D-Phe, His, D-His, Trp, D-Trp |
| Val | D-Val, Leu, D-Leu, Ile, D-Ile, Met, D-Met |

For example, some examples of conservative amino acid substitutions are listed in Table 2, and values greater than 0 represent that substitutions between two amino acids are conservative amino acid substitutions:

TABLE 2

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | -8 | -7 | -6 | -2 | -6 | -5 | -7 | -7 | -4 | -5 | -3 | -3 | 2 | -6 | -4 | -5 | -2 | 0 | 0 | 17 |
| Y | 0 | -5 | -5 | -3 | -3 | -3 | -4 | -4 | -2 | -4 | 0 | -4 | -5 | -2 | -2 | -1 | -1 | 7 | 10 | |
| F | -4 | -5 | -5 | -3 | -4 | -3 | -6 | -5 | -4 | -5 | -2 | -5 | -4 | -1 | 0 | 1 | 2 | 9 | | |
| L | -6 | -4 | -3 | -3 | -2 | -2 | -4 | -3 | -3 | -2 | -2 | -3 | -3 | 2 | 4 | 2 | 6 | | | |
| I | -2 | -3 | -2 | -1 | -1 | 0 | -2 | -2 | -2 | -2 | -2 | -2 | -2 | 4 | 2 | 5 | | | | |
| M | -5 | -3 | -2 | -2 | -1 | -1 | -3 | -2 | 0 | -1 | -2 | 0 | 0 | 2 | 6 | | | | | |
| V | -2 | -1 | -1 | -1 | 0 | 0 | -2 | -2 | -2 | -2 | -2 | -2 | -2 | 4 | | | | | | |
| R | -4 | -3 | 0 | 0 | -2 | -1 | -1 | -1 | 0 | 1 | 2 | 3 | 6 | | | | | | | |
| K | -5 | -2 | -1 | 0 | -1 | 0 | 0 | 0 | 1 | 1 | 0 | 5 | | | | | | | | |
| H | -3 | -2 | 0 | -1 | -1 | -1 | 1 | 1 | 2 | 3 | 6 | | | | | | | | | |
| Q | -5 | -1 | 0 | -1 | 0 | -1 | 2 | 2 | 1 | 4 | | | | | | | | | | |
| N | -4 | 0 | -1 | 1 | 0 | 0 | 2 | 1 | 2 | | | | | | | | | | | |
| E | -5 | 0 | -1 | 0 | 0 | 0 | 3 | 4 | | | | | | | | | | | | |
| D | -5 | 1 | -1 | 0 | 0 | 0 | 4 | | | | | | | | | | | | | |
| T | -2 | 0 | 0 | 1 | 1 | 3 | | | | | | | | | | | | | | |
| A | -2 | 1 | 1 | 1 | 2 | | | | | | | | | | | | | | | |
| S | 0 | 1 | 1 | 1 | | | | | | | | | | | | | | | | |
| P | -3 | -1 | 6 | | | | | | | | | | | | | | | | | |
| G | -3 | 5 | | | | | | | | | | | | | | | | | | |
| C | 12 | | | | | | | | | | | | | | | | | | | |

When forming the fusion protein of the invention, a linker or a connector may, but not necessarily, be used. When a linker is present, the chemical structure of it may be flexible since it primarily functions as a spacer. Linkers may be composed of amino acids linked together by peptide bonds. In some embodiments of the invention, the linker consists of 1 to 20 amino acids linked by peptide bonds. For example, the 1 to 20 amino acids are selected from the 20 natural amino acids. In some embodiments, the 1 to 20 amino acids are selected from glycine, serine, alanine, proline, asparagine, glutamine and lysine. In some embodiments, the linker consists of multiple amino acids that are spatially unhindered. For example, the spatially unhindered amino acids can be glycine and alanine. The linker may be a G-rich polypeptide, for example, which may be selected from (G) 3-S, i.e. "GGGS", (G) 4-S, i.e. "GGGGS" and (G) 5-S, i.e. "GGGGGS". In some embodiments, the linker comprises GGGGSGGGGS, GGGGSGGGGSGGGGS or GGGGSGGGGSGGGGSA. Other suitable linkers include GGGGGSGGGSGGGGS, GGGKGGGG, GGGNGSGG, GGGCGGGG, and GPNGG. The linker described herein can be a linker of any length or composition.

Linkers described above are exemplary, and the linker disclosed herein may be much longer and may contain other residues. The linker described herein may also be non-peptide linkers. For example, an alkyl linker can be used, such as $-NH-(CH_2)_s-C(O)-$, wherein s=2 to 20. These alkyl linkers may be further substituted with any non-sterically hindered group including, but not limited to, lower alkyl (e.g., C1-C6), lower acyl, halogen (e.g., Cl, Br), CN, $NH_2$ or phenyl. An exemplary non-peptidic linker can also be a polyethylene glycol linker, wherein the linker has a molecular weight of 100-5000 kD, such as 100-500 kD.

In the present application, "more" of the "one or more" amino acid substitutions generally refers to a substitution of more than one amino acid. For example from 1 to 30, 1 to 20, 1 to 10, 1 to 5, or such as 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 substitutions of amino acids.

In the present application, the "first" and "second" are only for the purpose of distinguishing the description and have no other meanings.

In the present application, the term "comprising" generally refers to the specified features but not excluding other elements.

In the present application, the term "protein" and "polypeptide" are used interchangeably and, in their broadest sense, refer to a compound consisting of two or more amino acids, amino acid analogs or peptidomimetic subunits. The two or more subunits can be linked by peptide bonds. In some embodiments, the two or more subunits can be linked by other bonds, such as esters, ethers, amino groups, and the like. The protein or polypeptide must contain at least two amino acids and there is no limit to the maximum number of amino acids that can make up the protein or peptide sequence. In the present application, the term "amino acid" generally refers to natural and/or unnatural or synthetic amino acids including D and L optical isomers of amino acids (such as glycine, D and L optical isomers thereof), amino acid analogs and peptide mimetics.

In the present application, the term "dimer" generally refers to a form of protein-protein interaction. For example, it can include a protein-protein complex composed of two related subunits. In the present application, the term "homologous dimer" generally refers to a dimer composed of two identical subunits, e.g., monomers.

In the present application, the term "homology" or "identity" or "similarity" are used interchangeably and generally refer to sequence similarity between two peptides or proteins or between two nucleic acid molecules. Homology can be determined by comparing the positions in each sequence that can be aligned for comparative purposes. When the positions in the sequences of the compared molecules are occupied by the same base or amino acid, these molecules are homologous at that position. The degree of homology between sequences varies with the number of matches or homologous positions shared by the sequences. An "unrelated" or "non-homologous" sequence indicates that there are less than 40% or 25% identities between the sequences being compared.

In the present application, when referring to the amino acid sequence identity of a polypeptide, the term "at least 80% sequence identity" generally refers to at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% sequence identity to each reference sequence.

In the present application, when used in connection with a numerical value, the term "about" generally include numerical values in the range having a lower limit of 5% less than the indicated value and an upper limit of 5% greater than the indicated value.

In the present application, the term "fusion protein" generally refers to a protein obtained by fusion of two or more proteins or polypeptides. A gene or nucleic acid molecule encoding two or more proteins or polypeptides can be joined to form a fusion gene or fusion nucleic acid molecule. The fusion gene or fusion nucleic acid molecule can encode the fusion protein. Translation of the fusion gene produces a single polypeptide having the property of at least one, or even each of the two or more proteins or polypeptides prior to fusion. Recombinant fusion proteins are artificially created by recombinant DNA techniques for biological research or therapy. In the present application, fusion proteins and recombinant fusion proteins are used interchangeably. The fusion proteins described herein generally comprise at least two domains, a linker between the two domains, and optionally a third component. Generation of recombinant fusion proteins is known in the art and generally involves removing the stop codon from the self-encoding the cDNA sequence of the first protein or polypeptide. The cDNA sequence for the second protein is then attached in-frame by ligation or overlap extension PCR. The DNA sequence is then expressed by the cell into a single protein. The protein can be engineered to include the complete sequence of two original proteins or polypeptides, or just a fraction of either.

As used in this specification and claims, the singular forms "a", "an" and "the" include plural referents unless the context clearly dictates otherwise. For example, the term "pharmaceutically acceptable carrier", "the pharmaceutically acceptable carrier" includes one or more pharmaceutically acceptable carriers, or a mixture thereof.

In the present application, the term "composition" generally refers to a combination of two or more substances, for example, a combination of the active agent with other inert or active compounds.

In the present application, the term "pharmaceutical composition" usually includes the active agent in combination with an inert or active carrier, so that the composition is suitable for diagnostic or therapeutic uses, either in vivo or in vitro or ex vivo.

In the present application, the term "therapeutically effective amount" generally refers to the minimum dose of active ingredient required to produce a therapeutic benefit in a subject. For example, for a patient exhibiting or susceptible to type II diabetes, obesity, or metabolic syndrome, or for preventing the onset of the disease, "therapeutically effective amount" refers to a dose that is capable of inducing, ameliorating, or causing a pathological condition, disease progression, or physiological condition that is associated with or counteracted by the disorder described above. In the present application, the term "subject" or "patient" may be a human, but may also be a non-human animal, more specifically may be a companion animal such as a dog, a cat or the like, a farm animal such as a cow, a sheep, a pig, horses, or laboratory animals such as rats, mice, guinea pigs, and the like.

In the present application, an expression of "XnY" indicates that residue X at position n in a sequence is substituted with residue Y when describing substitution of amino acid residues in the sequence. For example, amino acid substitution of "R175L" indicates that residue R at position 175 in a sequence is substituted with residue L.

FGF21 Variant

FGF21 has limited biological activity in vivo, and its hypoglycemic ability and lipid-lowering ability are not strong enough to make it a usable drug alone. In order to enhance its biological activity in reducing blood sugar and lipid, it is necessary to modify FGF21 and enhance its interaction with target protein thus enhancing its effect in vivo.

The inventors of the present application have surprisingly discovered that certain variant forms of human FGF21 are significantly capable of enhancing the ability of FGF21 to bind to its target.

In one aspect, the present application provides a FGF21 variant. The amino acid sequence of FGF21 variant includes one or more amino acid substitutions compared to the amino acid sequence shown in SEQ ID NO: 1, and the one or more amino acid substitutions comprise an amino acid substitution at position 167.

In some embodiments, the amino acid substitution at position 167 is S167H.

In some embodiments, the one or more amino acid substitutions further comprise amino acid substitutions at one or more positions selected from the group consisting of position 98, position 171, position 175, position 113, position 114, and position 135.

In some embodiments, the one or more amino acid substitutions comprise an amino acid substitution of L98R.

In some embodiments, the one or more amino acid substitutions comprise an amino acid substitution of P171A or P171G.

In some embodiments, the one or more amino acid substitutions comprise an amino acid substitution of R175L, R175P or R175H.

In some embodiments, the one or more amino acid substitutions comprise an amino acid substitution of G113R.

In some embodiments, the one or more amino acid substitutions comprise an amino acid substitution of L114Q.

In some embodiments, the one or more amino acid substitutions comprise an amino acid substitution of R135C.

In some embodiments, the one or more amino acid substitutions comprise amino acid substitutions selected from any one of the following combination of the amino acid positions: a) L98,␣S167 and P171; b) L98, S167, P171 and R175; and, c) L98, G113, L114, R135, S167, P171 and R175.

In some embodiments, amino acid substitutions comprise the amino acid sequence of any one of SEQ ID NO: 3-4 and SEQ ID NO: 26-27 is comprised.

In one aspect, the present application provides a FGF21 variant which comprises the amino acid sequence of SEQ ID NO: 2.

(SEQ ID NO: 2)
HPIPDSSPLLQFGGQVRQRYLYTDDAQQTEAHLEIREDGTVGGAADQSPE

SLLQLKALKPGVIQILGVKTSRFLCQRPDGALYGSLHFDPEACSFRELLE

DGYNVYQSEAHX$_2$X$_3$PLHLPGNKSPHRDPAPRGPAX$_4$FLPLPGLPPALPEP

PGILAPQPPDVGSSDPLX$_5$MVGX$_6$SQGX$_7$SPSYAS,

Wherein $X_1$ is L, R, D, E or K; $X_2$ is G or R; $X_3$ is L or Q; $X_4$ is R or C; $X_5$ is S, C, R or H; and $X_6$ is P, C, G or A; $X_7$ is R, H, P or L; wherein the FGF21 variant comprises at least one amino acid substitution selected from $X_1$ to $X_7$ compared to native FGF21, and the amino acid sequence of the natural FGF21 is shown in SEQ ID NO: 1.

In some embodiments, the FGF21 variant at least comprises an amino acid substitution at position 167 ($X_5$) and/or at position 175 ($X_7$) compared to natural FGF21. For example, based on the native FGF21 sequence (SEQ ID NO: 1), the FGF21 variant (SEQ ID NO: 2) at least comprises an amino acid substitution at position 167 ($X_5$), an amino acid substitution at position 175 ($X_7$) or amino acid substitutions at positions 167 ($X_5$) and 175 ($X_7$).

The amino acid substitution at position 167 may be selected from S167H, S167C and S167R. The amino acid substitution at position 175 may be selected from the R175L, R175H and R175P. In some embodiments, the amino acid substitution at position 167 is selected from S167H, S167C and S167R, and the amino acid substitution at position 175 is selected from R175L, R175H and R175P. In some embodiments, the amino acid substitution at position 167 is S167H, and the amino acid substitution at position 175 is selected from R175L, R175H and R175P. In certain embodiments, the amino acid substitution at position 167 is S167H, and the amino acid substitution at position 175 is R175L.

In certain embodiments, the FGF21 variant (e.g., having an amino acid sequence of SEQ ID NO: 2) described herein at least comprises an amino acid substitution at position 98 (e.g., $X_1$ in SEQ ID NO: 2) and/or at position 171 (e.g., $X_6$ in SEQ ID NO: 2). For example, based on the native FGF21 sequence (SEQ ID NO: 1), the FGF21 variant (SEQ ID NO: 2) at least comprises an amino acid substitution at position 98 ($X_1$), an amino acid substitution at position 171 ($X_6$) or amino acid substitutions at positions 98 ($X_1$) and 171 ($X_6$).

The amino acid substitution at position 98 may be selected from the group consisting of L98D, L98R, L98E and L98K. The amino acid substitution at position 171 may be selected from the group consisting of P171A, P171C and P171G. In some embodiments, the amino acid substitution at position 98 is selected from the group consisting of L98D, L98R, L98E and L98K, and the amino acid substitution at position 171 is selected from the group consisting of P171A, P171C and P171G. In some embodiments, the amino acid substitution at position 98 is L98R, and the amino acid substitution at position 171 is selected from the group consisting of P171A and P171G.

In certain embodiments, the FGF21 variant (e.g., having an amino acid sequence of SEQ ID NO: 2) described herein comprises an amino acid substitution at position 167 and/or at position 175 ($X_7$), as well as an amino acid substitution at position 98 (e.g., $X_1$ in SEQ ID NO:2) and/or at position 171 (e.g., X6 in SEQ ID NO:2). For example, based on the native FGF21 sequence (SEQ ID NO: 1), the FGF21 variant (SEQ ID NO: 2) at least comprises an amino acid substitution at position 167 ($X_5$) and an amino acid substitution at position 98 ($X_1$). Another example, based on the native FGF21 sequence (SEQ ID NO: 1), the FGF21 variant (SEQ ID NO: 2) at least comprises an amino acid substitution at position 167 ($X_5$) and an amino acid substitution at position 171 ($X_6$). In certain embodiments, based on the native FGF21 sequence (SEQ ID NO: 1), the FGF21 variant (SEQ ID NO: 2) at least comprises an amino acid substitution at position 167 ($X_5$), an amino acid substitution at position 171 ($X_6$) and an amino acid substitution at position 98 ($X_1$). In certain embodiments, based on the native FGF21 sequence (SEQ ID NO: 1), the FGF21 variant (SEQ ID NO: 2) at least comprises an amino acid substitution at position 175 ($X_7$) and an amino acid substitution at position 98 ($X_1$). In certain embodiments, based on the native FGF21 sequence (SEQ ID NO: 1), the FGF21 variant (SEQ ID NO: 2) at least comprises an amino acid substitution at position 175 ($X_7$) and an amino acid substitution at position 171 ($X_6$). In certain embodiments, based on the native FGF21 sequence (SEQ ID NO: 1), the FGF21 variant (SEQ ID NO: 2) at least comprises an amino acid substitution at position 175 ($X_7$), an amino acid substitution at position 98 ($X_1$) and an amino acid substitution at position 171 ($X_6$). In certain embodiments, based on the native FGF21 sequence (SEQ ID NO: 1), the FGF21 variant (SEQ ID NO: 2) at least comprises an amino acid substitution at position 175 ($X_7$), an amino acid substitution at position 167 ($X_5$) and an amino acid substitution at position 171 ($X_6$). In certain embodiments, based on the native FGF21 sequence (SEQ ID NO: 1), the FGF21 variant (SEQ ID NO: 2) at least comprises an amino acid substitution at position 175 ($X_7$), an amino acid substitution at position 167 ($X_5$) and an amino acid substitution at position 98 ($X_1$). In certain embodiments, based on the native FGF21 sequence (SEQ ID NO: 1), the FGF21 variant (SEQ ID NO: 2) at least comprises an amino acid substitution at position 175 ($X_7$), an amino acid substitution at position 167 ($X_5$), an amino acid substitution at position 171 ($X_6$) and an amino acid substitution at position 98 ($X_1$).

In some embodiments, the FGF21 variant (e.g., having an amino acid sequence of SEQ ID NO: 2) described herein further comprises amino acid substitutions at position 113 (e.g., $X_2$ in SEQ ID NO: 2), at position 114 (e.g., $X_3$ in SEQ ID NO: 2), and/or at position 135 (e.g., $X_4$ in SEQ ID NO: 2). The amino acid substitutions at position 113($X_2$) can be G113R. The amino acid substitutions at position 114($X_3$) can be L114Q. The amino acid substitutions at position 135($X_4$) can be R135C.

In certain embodiments, the FGF21 variant (e.g., having an amino acid sequence of SEQ ID NO: 2) described herein comprises amino acid substitutions at position 167 and/or at position 175 ($X_7$), and/or amino acid substitutions at position 98 (e.g., $X_1$ in SEQ ID NO:2) and/or at position 171 (e.g., $X_6$ in SEQ ID NO:2), as well as amino acid substitutions at position 113 (e.g., $X_2$ in SEQ ID NO:2), at position 114 (e.g., $X_3$ in SEQ ID NO:2) and/or at position 135 (e.g., $X_4$ in SEQ ID NO:2).

In certain embodiments, based on the native FGF21 sequence (SEQ ID NO: 1), the FGF21 variant (SEQ ID NO: 2) comprises amino acid substitutions at position 167 ($X_5$), position 175 ($X_7$), position 98 ($X_1$), position 171 ($X_6$), position 113 ($X_2$), position 114 ($X_3$) and position 135 ($X_4$).

In some embodiments, the FGF21 variant described herein comprises the amino acid sequence of any one of SEQ ID NO: 3-4 and SEQ ID NO: 34-37.

Fusion Protein and Protein Multimer

In another aspect, the application provides a fusion protein comprising a FGF21 variant described herein. The fusion protein may also comprise an IgG constant region domain or a fragment thereof, and the IgG constant region domain or the fragment thereof fuses with the FGF21 variant to form the fusion protein.

The fragment of the IgG constant region domain can be a portion of an IgG constant region domain, but still retain at least a portion of its activity. In some embodiments, the IgG constant region domain or the fragment thereof comprises or is an IgG4 Fc domain.

In some embodiments, the IgG4 Fc domain may comprise the amino acid sequence of SEQ ID NO: 5 or SEQ ID NO: 6. In certain embodiments, the FGF21 variant is fused to the IgG constant region domain or the fragment thereof by a linker. For example, the N-terminus of the FGF21 variant is directly or indirectly linked to the C-terminus of the IgG constant region domain or the fragment thereof. In some embodiments, the N-terminus of the FGF21 variant is linked to the C-terminus of the IgG constant region domain or the fragment thereof by a first linker. The first linker may comprise the amino acid sequence of GGGGSGGGGSGGGGS (SEQ ID NO: 7) or GGGGSGGGGSGGGGSA (SEQ ID NO: 8).

In certain embodiments, the fusion protein may comprises the amino acid sequence of any one of SEQ ID NO: 9, SEQ ID NO: 10, SEQ ID NO: 11, SEQ ID NO: 12, SEQ ID NO: 13, SEQ ID NO: 14, SEQ ID NO: 26 and SEQ ID NO: 27.

In certain embodiments, the fusion protein described herein further comprises GLP-1 receptor agonist portion. The GLP-1 receptor agonist portion may comprise GLP-1 analogues. In some embodiments, the GLP-1 analogs comprise the amino acid sequence of SEQ ID NO: 15 or SEQ ID NO: 28:

In some embodiments, the fusion protein comprises the FGF21 variant, the IgG constant region domain or the fragment thereof and the GLP-1 receptor agonist portion described herein. In certain embodiments, the C-terminus of the GLP-1 receptor agonist portion is directly or indirectly linked to the N-terminus of the IgG constant region domain or the fragment thereof. In some embodiments, the C-terminus of the GLP-1 receptor agonist portion is linked to the N-terminus of the IgG constant region domain or the fragment thereof by a second linker. In some embodiments, the C-terminus of the GLP-1 receptor agonist portion is linked to the N-terminus of the IgG constant region domain or the fragment thereof by a second linker, and the N-terminus of the FGF21 variant is linked to the C-terminus of the IgG constant region domain or the fragment thereof by a first linker. The first linker and the second linker may independently comprise the amino acid sequence of SEQ ID NO: 7 or SEQ ID NO: 8, respectively.

In some embodiments, the fusion protein comprises the amino acid sequence of any one of SEQ ID NO: 16-18.

In another aspect, the application provides a protein multimer comprising two or more fusion proteins described herein. In some embodiments, the protein multimer is a homodimer. For example, the protein multimer can be composed of two identical fusion proteins described herein. In certain embodiments, two or more monomers (i.e., two or more fusion proteins described herein) of the protein polymer constitute the protein polymer mainly by non-covalent interactions and/or disulfide bonds binding to each other.

The FGF21 variant, the fusion protein, the protein multimer or composition (e.g., pharmaceutical composition) described herein can be used to treat metabolic diseases. The metabolic diseases are selected from diabetes, obesity and hepatic steatosis. In some embodiments, the metabolic disease is diabetes, such as type II diabetes. In other embodiments, the metabolic disease is obesity. Other embodiments include metabolic conditions or metabolic disorders such as dyslipidemia, hypertension, hepatic steatosis, such as non-alcoholic fatty liver disease (NASH), cardiovascular diseases such as atherosclerosis, and aging.

Nucleic Acid Molecules, Vectors and Cells

In another aspect, the application provides an isolated nucleic acid molecule encoding the FGF21 variant or the fusion protein described herein.

The nucleic acid molecule may be in the form of RNA, or in the form of DNA, wherein DNA includes cDNA and synthetic DNA. DNA can be double-stranded or single-stranded. The coding sequence encoding the FGF21 variant or fusion protein of the present application may differ due to the result of the redundancy or degeneracy of the genetic code. The nucleic acid molecule may comprise: only a coding sequence of a protein; a coding sequence of a protein and coding sequences of other parts, such as a leader sequence or a secretory sequence or a preprotein sequence; a coding sequence and a non-coding sequence of a protein, such as 5' and/or 3' non-coding sequences of a coding sequence of an intron or a protein, etc. Thus, the term "nucleic acid molecule encoding a protein" encompasses such a polynucleotide which may not only include the coding sequence of a protein or polypeptide, but also include coding sequences and/or non-coding sequences of other portions.

In some embodiments, the isolated nucleic acid comprises the amino acid sequence of any one of SEQ ID NO: 19, SEQ ID NO: 20, SEQ ID NO: 21, SEQ ID NO: 22, SEQ ID NO: 23, SEQ ID NO: 24 and SEQ ID NO: 25.

In another aspect, the application provides a vector comprising the nucleic acid molecule described herein. The vector (e.g., an expression vector) can usually replicate in the host organism as an episome or as part of the host chromosomal DNA. Generally, expression vectors may contain selectable markers, such as tetracycline, neomycin, and dihydrofolate reductase, so that detection of those cells converted by the desired nucleic acid molecule is allowed. For example, the pcDNA3.4 vector.

In another aspect, the application also provides a cell (e.g., a host cell) comprising the vector described herein. The cell may include, such as mammalian cell (e.g., CHO, NSO, HEK293, or COS cell); bacterial cell (e.g., *Escherichia coli, Bacillus subtilis, Pseudomonas* fluorescence); or fungal or yeast cell. In certain embodiments, the cell is a HEK293 cell or a CHO cell.

In another aspect, the application also provides a method for preparing the FGF21 variant described herein, the fusion protein described herein or the protein multimer described herein. The method comprises culturing the cell described herein under conditions that permits expression and/or formation of the FGF21 variant, the fusion protein or the protein multimer. In certain embodiments, the method further comprises recovering the expressed and/or formed FGF21 variant, the fusion protein, or the protein multimer. The vector containing the objective nucleic acid molecule can be transferred to a cell (e.g., a host cell) by a well-known method, and such a method differs depending on the type of the cell. For example, calcium chloride conversion is commonly used in prokaryotic cells, while calcium phosphate treatment or electroporation can be used in other host cells. In general, the principles, methods, and practical technologies for maximizing cell culture productivity can be found in the works of *Mammalian Cell Biotechnology: A Practical Approach*, edited by M. Butler (IRL Press, 1991) and Sambrook et al.

In another aspect, the application provides a composition (e.g., a pharmaceutical composition) comprising the FGF21 variant described herein, the fusion protein described herein or the protein multimer described herein, and optionally one or more pharmaceutically acceptable carriers, adjuvants or excipients. The composition may comprises a therapeutically effective amount of the FGF21 variant described herein, the fusion protein described herein or the protein multimer described herein.

The pharmaceutically acceptable carrier, adjuvant or excipient is preferably non-toxic to the subject at the used dosages and concentrations.

The composition may contain a formulation for changing, maintaining or preserving, such as, the pH of the composition, osmolality, viscosity, transparency, color, isotonicity, odor, sterility, stability, dissolution or release rate, absorption or permeation. Suitable composition formulations can be determined by technicians based on, such as the intended route of administration, the mode of delivery, and the desired dosage (see, for example, Remington's Pharmaceutical Sciences).

The FGF21 variant, fusion protein or protein multimer composition can be selected for parenteral delivery. Alternatively, the composition can be selected for inhalation or for delivery through the digestive tract, for example, orally. The preparation of such pharmaceutically acceptable compositions is known to those skilled in the art.

When parenteral administration is contemplated, the composition for used herein may be a pyrogen-free, parenterally acceptable aqueous solution containing a desired FGF21 variant, a fusion protein or a protein multimer, and a pharmaceutically acceptable vehicle. A particularly suitable vehicle for parenteral injection is sterile distilled water, wherein the FGF21 variant, fusion protein or protein multimer is formulated into a suitably preserved sterile isotonic solution. Yet another preparation may include a preparation of a desired molecule with a substance such as injectable microspheres, biodegradable particles, polymers (e.g., polylactic acid or polyglycolic acid), beads or liposomes. The substance is provided for a controlled or sustained release product which can then be delivered by a depot injection. Hyaluronic acid can also be used, which has the effect on promoting prolonged duration in the circulation. Other suitable methods for introducing the desired molecule include implantable drug delivery devices.

In one embodiment, the composition can be formulated for inhalation. For example, the FGF21 variant, fusion protein or protein multimer described herein can be made into a dry powder for inhalation. The inhalation solution of the FGF21 variant, fusion protein or protein multimer can also be formulated with propellants for aerosol delivery. In yet another embodiment, the solution can be atomized. Pulmonary administration is described more in International Publication No. WO 94/20069, which describes pulmonary delivery of chemically modified proteins.

It is also contemplated that certain formulations may be administered orally. In one embodiment of the present application, the FGF21 variant, fusion protein or protein multimer administered in this manner may be formulated with or without carriers commonly used in formulating solid dosage forms such as tablets and capsules. For example, a capsule can be designed to release the active portion of the formulation at a point where bioavailability of the gastrointestinal tract is maximized and pre-systemic degradation is minimized. Other substances that promote the absorption of the FGF21 variant, fusion protein or protein multimer may be included. Diluents, flavoring agents, low melting waxes, vegetable oils, lubricants, suspending agents, tablet disintegrating agents, and binders can also be used.

Another composition may comprise an effective amount of a mixture of the FGF21 variant, fusion protein or protein multimer and a non-toxic excipient suitable for preparation of tablet. Solutions are prepared in unit dosage form by dissolving the tablet in sterile water or another suitable vehicle.

Other types of FGF21 variant, fusion protein or protein multimer compositions may also be provided, for example, including formulations comprising FGF21 variants, fusion proteins or protein multimers in sustained delivery or controlled delivery formulations. Techniques for preparing a variety of other sustained delivery or controlled delivery vehicles, such as liposome carriers, biodegradable particulates or porous beads, and depot injections, are also known to those skilled in the art (see, for example, International Publication No. WO 93/15722, which disclosed controlled release of porous polymeric microparticles for delivery of pharmaceutical compositions, as well as Wischke & Schwendeman, 2008, Int. J. Pharm. 364:298-327, and Freiberg & Zhu, 2004, Int. J. Pharm. 282:1-18, which discussed microsphere/microparticle formulations and uses thereof). As described herein, a hydrogel is an example of a sustained delivery or controlled delivery formulation.

The FGF21 variant, fusion protein or protein multimer composition administrated in vivo generally should be sterile. This can be achieved by filtration with a sterile filter membrane. If the composition is lyophilized, sterilization by this method can be carried out before or after lyophilization and reconstitution. Compositions for parenteral administration may be stored in lyophilized form or in solution. Additionally, parenteral compositions are generally enclosed in a container having a sterile inlet, such as a solution bag or vial for intravenous injection with a stopper punctured by a hypodermic needle.

Once formulated into composition, it can be stored as a solution, suspension, gel, emulsion, solid, or as a dehydrated powder or lyophilized powder in a sterile vial. Such formulations can be stored in a ready-to-use form or in a form which requires reconstitution prior to administration (e.g., in a lyophilized form).

In certain embodiments, the application relates to a kit for producing an administration unit of single dose. The kit can each contain both a first container having a dried protein and a second container having a water-containing formulation. The scope of the present application also includs a kit comprising a single chamber prefilled syringe and a multi-chamber prefilled syringe (e.g., a syringe of liquid dose and a syringe of lyophilized powder).

Administration route of the pharmaceutical composition is consistent with known methods, such as oral administration; by intravenous, intraperitoneal, intracerebral (intracerebral parenchyma), intraventricular, intramuscular, intraocular, intraarterial, portal vein or intralesional injection; by a sustained release system (which can also be injected); or by an implant device. If desired, the composition can be administered by bolus or continuous infusion, or by an implant device.

Alternatively or additionally, the composition can be administered topically by implantation of a film, sponge or other suitable material onto which the desired active ingredient has been absorbed or encapsulated. When the implant device is used, the device can be implanted into any suitable tissue or organ and the desired active ingredient can be delivered by diffusion, timed-release bolus or continuous administration.

The composition can be used to treat metabolic diseases. In some embodiments, the metabolic disease is diabetes, such as type II diabetes. In other embodiments, the metabolic disease is obesity. Other embodiments include metabolic conditions or metabolic disorders such as dyslipidemia, hypertension, hepatic steatosis, such as non-alcoholic fatty liver disease (NASH), cardiovascular diseases such as atherosclerosis, and aging.

In another aspect, the present application also provides the following embodiments:

1. The amino acid sequence of the FGF21 variant includes one or more amino acid substitutions compared to the amino acid sequence shown in SEQ ID NO: 1, the one or more amino acid substitutions comprising an amino acid substitution at position 167, wherein the amino acid substitution at position 167 is S167H.

2. The FGF21 variant of embodiment 1, wherein the one or more amino acid substitutions further comprise amino acid substitutions at one or more positions selected from the group consisting of position 98, position 171, position 175, position 113, position 114, and position 135.

3. The FGF21 variant of embodiment 2, wherein the one or more amino acid substitutions comprise an amino acid substitution of L98R.

4. The FGF21 variant of any one of embodiments 2 to 3, wherein the one or more amino acid substitutions comprise an amino acid substitution of P171A or P171G.

5. The FGF21 variant of any one of embodiments 2 to 4, wherein the one or more amino acid substitutions comprise amino acid substitutions of R175L, R175P and R175H.

6. The FGF21 variant of any one of embodiments 2 to 5, wherein the one or more amino acid substitutions comprise an amino acid substitution of G113R.

7. The FGF21 variant of any one of embodiments 2 to 6, wherein the one or more amino acid substitutions comprise an amino acid substitution of L114Q.

8. The FGF21 variant of any one of embodiments 2 to 7, wherein the one or more amino acid substitutions comprise an amino acid substitution of R135C.

9. The FGF21 variant of any one of embodiments 1 to 8, wherein the one or more amino acid substitutions comprise an amino acid substitution selected from any one of the following combination of the amino acid positions:
 a) L98, S167 and P171;
 b) L98, S167, P171 and R175; and,
 c) L98, G113, L114, R135, S167, P171 and R175.

10. The FGF21 variant of any one of embodiments 1 to 9, which comprises the amino acid sequence of any one of SEQ ID NO: 3-4 and SEQ ID NO: 34-37.

11. A fusion protein comprising the FGF21 variant of any one of embodiments 1 to 10.

12. The fusion protein of embodiment 11, which further comprises an IgG constant region domain or a fragment thereof.

13. The fusion protein of embodiment 12, wherein the IgG constant region domain or the fragment thereof comprises an IgG4 Fc domain.

14. The fusion protein of embodiment 13, wherein the IgG4 Fc domain comprises the amino acid sequence of any one of SEQ ID NO: 5-6.

15. The fusion protein of any one of the embodiments 12 to 14, wherein the N-terminus of the FGF21 variant is directly or indirectly linked to the C-terminus of the IgG constant region domain or the fragment thereof.

16. The fusion protein of embodiment 15, wherein the N-terminus of the FGF21 variant is directly or indirectly linked to the C-terminus of the IgG constant region domain or the fragment thereof by a first linker.

17. The fusion protein of embodiment 16, wherein the first linker comprises the amino acid sequence of any one of SEQ ID NO: 7-8.

18. The fusion protein of any one of embodiments 11 to 17, which comprises the amino acid sequence of any one of SEQ ID NO: 9-14 and SEQ ID NO: 26-27.

19. The fusion protein of any one of embodiments 11 to 18, which further comprises a GLP-1 receptor agonist portion.

20. The fusion protein of embodiment 19, wherein the GLP-1 receptor agonist portion comprises a GLP-1 analogue.

21. The fusion protein of any one of embodiments 19 to 20, wherein the GLP-1 receptor agonist portion comprises the amino acid sequence of any one of SEQ ID NO: 15 and SEQ ID NO: 28.

22. The fusion protein of any one of embodiments 19 to 21, which comprises the IgG constant region domain or the fragment thereof and the GLP-1 receptor agonist portion, and the C-terminus of the GLP-1 receptor agonist portion is directly or indirectly linked to the N-terminus of the IgG constant region domain or the fragment thereof.

23. The fusion protein of embodiment 22, wherein C-terminus of the GLP-1 receptor agonist portion is linked to the N-terminus of the IgG constant region domain or the fragment thereof by a second linker.

24. The fusion protein of embodiment 23, wherein the second linker comprises the amino acid sequence of any one of SEQ ID NO: 7-8.

25. The fusion protein of any one of embodiments 19 to 24, which comprises the IgG constant region domain or the fragment thereof, the GLP-1 receptor agonist portion, and the FGF21 variant, and the N-terminus of the FGF21 variant is directly or indirectly linked to the C-terminus of the IgG constant region domain or the fragment thereof.

26. The fusion protein of embodiment 25, the C-terminus of the GLP-1 receptor agonist portion is linked to the N-terminus of the IgG constant region domain or the fragment thereof by a second linker, and the N-terminus of the FGF21 variant is linked to the C-terminus of the IgG constant region domain or the fragment thereof by a first linker.

27. The fusion protein of any one of embodiments 25 to 26, which comprises the amino acid sequence of any one of SEQ ID NO: 16-18.

28. A protein multimer comprising two or more fusion proteins of any one of embodiments 11 to 27.

29. The protein multimer of embodiment 28, which is a homodimer.

30. An isolated nucleic acid molecule encoding the FGF21 variant of any one of embodiments 1 to 10 or the fusion protein of any one of embodiments 11 to 27.

31. A vector comprising the isolated nucleic acid molecule of embodiment 30.

32. A cell comprising the vector of embodiment 31.

33. A method of preparing the FGF21 variant of any one of embodiments 1 to 10, the fusion protein of any one of embodiments 11 to 27 or the protein multimer of any of embodiments 28 to 29, wherein the method comprises culturing the cell of embodiment 32 under conditions that permits expression and/or formation of the FGF21 variant, the fusion protein or the protein multimer.

34. The method of embodiment 33, which further comprises recovering the expressed and/or formed FGF21 variant, the fusion protein, or the protein multimer.

35. A pharmaceutical composition comprising the FGF21 variant of any one of embodiments 1 to 10, the fusion protein of any one of embodiments 11 to 27 or the protein multimer of any one of embodiments 28-29, and optionally one or more pharmaceutically acceptable carriers.

36. Use of the FGF21 variant of any one of embodiments 1 to 10, the fusion protein of any one of embodiments 11 to 27 or the protein multimer of any one of embodiments 28 to 29 in the manufacture of a medicament for treating metabolic diseases.

37. Use according to embodiment 36, wherein the metabolic diseases are selected from diabetes, obesity and hepatic steatosis.

38. The FGF21 variant of any one of embodiments 1 to 10, the fusion protein of any one of embodiments 11 to 27 or the protein multimer of any one of embodiments 28 to 29 for use in treating metabolic diseases.

39. The FGF21 variant, the fusion protein or the protein multimer of embodiment 38, wherein the metabolic diseases are selected from diabetes, obesity and hepatic steatosis.

40. A method of treating metabolic diseases comprising administering a therapeutically effective amount of the FGF21 variant of any one of embodiments 1 to 10, the fusion protein of any one of embodiments 11 to 27 or the protein multimer of any one of embodiments 28 to 29 to the patient.

41. The method of embodiment 40, wherein the metabolic diseases are selected from diabetes, obesity and hepatic steatosis.

Examples

The present application is further understood by the following examples, which are merely examples of the disclosure. The present application is not to be limited in scope by the illustrated embodiments, which are merely intended to illustrate a single aspect of the present invention. Any method that is functionally equivalent is included in the scope of the present invention. From the above description and the drawings, various modifications of the invention in addition to those described herein will be apparent to those skilled in the art. These modifications are also within the scope of the claims.

Example 1 Construction of Expression Vector of Fusion Protein S1-S8

TABLE 3

| Code of fusion protein | Amino acid substitution in FGF21 variant | Fusion protein SEQ ID NO: | FGF21 variant SEQ ID NO: |
| --- | --- | --- | --- |
| S1 | 98R, 167H, 171A | 9 | 34 |
| S2 | 98R, 167H, 171A, 175L | 10 | 3 |
| S3 | 98R, 167H, 171G, 175L | 11 | 4 |
| S4 | 98R, 167H, 171A, 175P | 12 | 35 |
| S5 | 98R, 167H, 171A, 175H | 13 | 36 |
| S6 | 98R, 113R, 114Q, 135C, 167H, 171A, 175P | 14 | 37 |
| S7 | 98R, 171A | 26 | — |
| S8 | 98R, 171G | 27 | — |

The objective gene was synthesized by Suzhou Genewiz Biological Technology Co., Ltd. The 5' end of the objective gene contains a Fc of human IgG4, a linker and a FGF21 variant in turn, and the amino acid sequence of the fusion protein S1-S7 encoded by the objective gene was shown in Table 3. The sequence of the objective gene and the vector plasmid pcDNA3.4 were digested with the endonuclease HindIII and EcoRI (TAKARA, Japan) at 37° C., and the digested product was purified and recovered by using a Gel Extraction Kit according to the manufacturer's instructions. The purified objective gene was ligated with the vector using a DNA Ligation Kit Ver.2.1 (TAKARA, Japan) according to the manufacturer's instructions and incubated at 16° C. for 1 hour to obtain a recombinant expression plasmid.

The above recombinant expression plasmid was transformed into competent cells DH5a, and bacteria was coated into an ampicillin plate. The monoclonal on the plate was picked and cultured in 1 ml of LB medium (peptone 10 g/L, yeast extract 5 g/L, sodium chloride 10 g/L and agar 2%, antibiotic content 100 µg/mL) to extract the plasmid. After sequencing and validation by Guangzhou Aiji Biotechnology Co., Ltd., a series of validated correct expression vectors were extracted with Invitrogen Plasmid Kit and digested with restriction enzyme PvuI (TAKARA, Japan). After linearization, the product was purified and recovered by ethanol precipitation method and stored at −20° C. for future use.

Example 2 Expression of Fusion Protein S1-S8

HEK293F host cells (Invitrogen, Freestyle 293F) were resuscitated with 293 Expression Medium. The host cells were transfected when the cell density was about $1 \times 10^6$ cells/mL. About $3 \times 10^7$ cells were transfected, and the linearized expression vector prepared in Example 1 was about 37.5 µg. The cells were transfected with FreeStyle™ MAX Reagent Transfection Kit. After transfection, the cells were cultured in 30 mL of 293 Expression Medium. On the second day of culture, transformants were started to be screened with geneticinG418 (merck). The medium was replaced every 3 days depending on the growth of the cells. After about 14 days of selection, resistant clones appeared and could be expanded. The cell passage density was about $0.5 \times 10^6$ cells/mL. The obtained mixed clone was subcultured with 293 Expression Medium. When the cell viability was about 90%, the cell culture fluid was collected.

Example 3 Purification of Fusion Protein S1-S8

Figure 12:
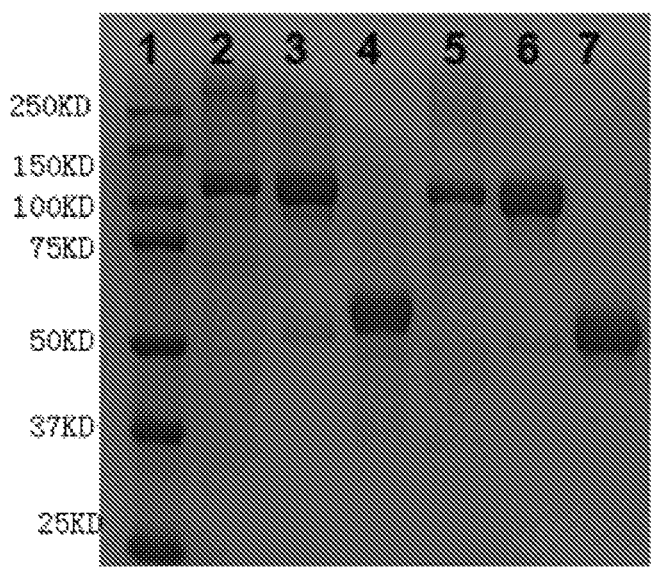
FIG. 12 shows the results of purification of the fusion proteins S2 and D2 of the present application.

The cell culture solution prepared in Example 2 was centrifuged at 200 g for 10 min, and the supernatant was centrifuged at 8000 rpm for 30 min, and the supernatant was collected. The collected cell culture supernatant was subjected to affinity purification by Protein A chromatography (EzFast Protein A Diamond, Bestchrom). The equilibration solution was 20 mM PBS, 0.15 M NaCl, pH 7.4. The eluent was 0.1 M citric acid-sodium citrate buffer of pH 3.2. The target eluate was collected at target absorption peak and dialyzed with PBS buffer to take part of the sample for mass spectrometry. Mass spectrometry detection molecular weight was consistent with theoretical molecular weight, and they were in homodimeric form. At the same time, the collected samples were detected by 10% SDS-PAGE electrophoresis after reduction and non-reduction. The fusion protein S2 is taken as an example, and the purification result thereof is shown in FIG. 12. The first band is a protein molecular weight marker, the fifth band is fermentation supernatant of the fusion protein S2, the sixth band is the purified fusion protein S2, and the seventh lane is the reduced fusion protein S2.

Example 4 Method of ELISA for Detecting the Binding Ability of Fusion Protein to Target Firstly, 10 μg of βKlotho protein (AVIVA SYSTEMS BIOLOGY) was dissolved in 10 ml of a protein coating solution (carbonate buffer of pH 9.6). After mixing, 100 μL of the mixture was added to each well of the ELISA plate, and placed overnight at 4° C. Then, the coating solution was removed, and washed 4 times with PBST solution. 200 μL of blocking solution (5 g of skim milk powder added into 100 ml of PBS solution) was added into each well, and incubated at 37° C. After 2 h, the blocking solution was removed. 100 μL of the fusion protein samples at different concentrations were added into each well. Then the plate was sealed in a ziplock bag and placed at 37° C. After 2 h, each well was washed 4 times with PBST solution. 100 μL of Anti-Human IgG 4 Fc-HRP (1/1000) (Abcam) was added and incubated for 1 h at 37° C. Finally, each well was washed 4 times with PBST solution. 100 μL of highly sensitive TMB substrate was added, and after 2 min, 50 μL of stop solution (2M $H_2SO_4$) was added to stop the reaction. The OD value of each well was measured by a microplate reader.

Figure 3:
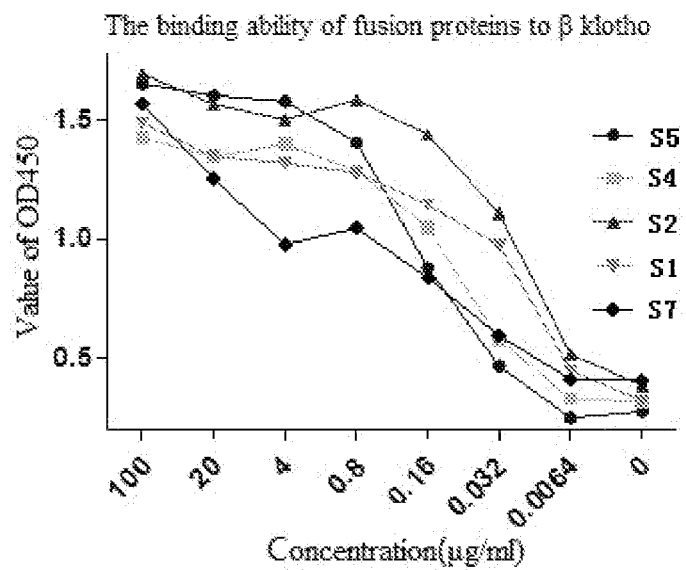
FIG. 3 shows the binding ability of the fusion proteins S5, S4, S2, 51 and S7 of the present application to β klotho.
Figure 4:
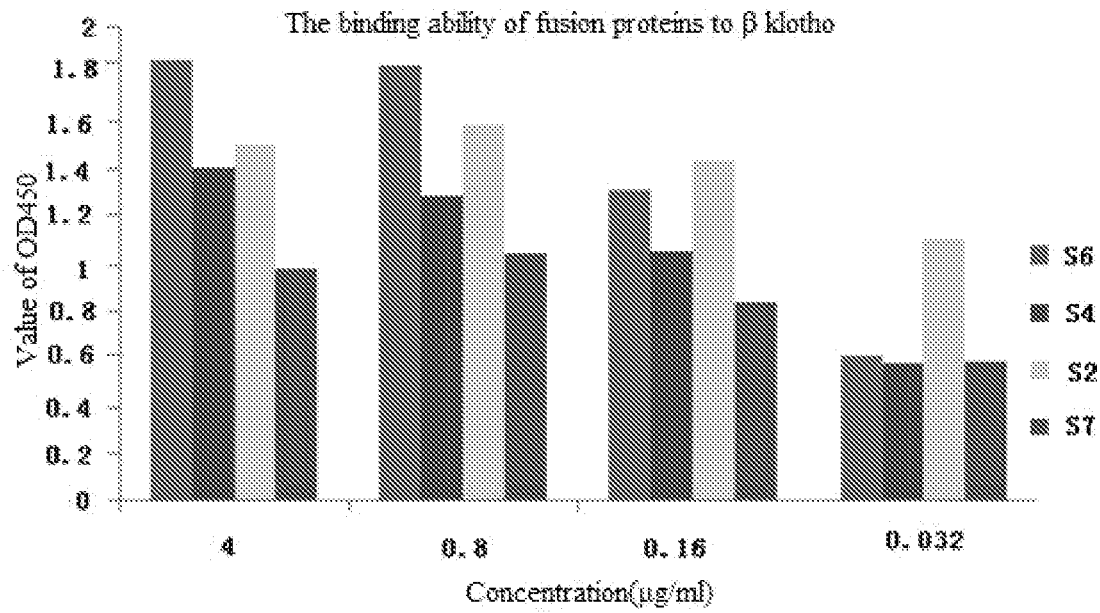
FIG. 4 shows the binding ability of the fusion proteins S6, S4, S2 and S7 of the present application to β klotho.

The results are shown in FIG. 3 and FIG. 4. FIG. 3 shows that the binding ability of fusion protein S7 to target decreases significantly with the decrease of concentration. Compared with S7, the binding ability of fusion protein S1/S2/S4/S5 to target increases significantly with the increase of amino acid substitutions at position 167 and/or 175. The binding ability to the target of S1\S2\S4\S5 in the concentration range of 100 μg/mL-0.8 μg/mL can be maintained at a high level, indicating that position 167 and position 175 are closely related to the target binding ability. FIG. 4 shows that the binding ability of fusion protein to target remains at a high level with the increase of amino acid substitutes at position 113, position 114 and position 135.

Example 5 Method of Fortebio for Detecting the Binding Ability of Fusion Protein to Target Each fusion protein sample was diluted to 40 nM with buffer (0.1 g of BSA added into 100 ml of PBS buffer and stirred until fully dissolved, and then 20 μL of Tween 20 added, mixed), and added into each well of the sample plate. After the biotinylated βKlotho (25 nM, AVIVA SYSTEMS BIOLOGY) protein binding with a probe of streptavidin, the binding condition to each fusion protein was automatically detected by an affinity detection system (OCTET RED 96 SYSTEM). The results are shown in Table 4. The lower the KD value, the stronger the binding ability of the fusion protein to the target. Table 4 shows that compared with the fusion protein S7, the binding ability of fusion protein 51 to the target is greatly improved by adding amino acid substitute at position 167. After further increasing the amino acid substitution at position 175, such as the fusion protein S2, the binding ability to target is twice as strong as that of S7.

TABLE 4

| Fusion protein sample | SEQ ID NO: | Concentration (nM) | Response values | KD (M) |
|---|---|---|---|---|
| S1 | 9 | 40 | 0.1695 | $6.30 \times 10^{-10}$ |
| S7 | 26 | 40 | 0.1428 | $8.73 \times 10^{-10}$ |
| S2 | 10 | 40 | 0.1898 | $4.29 \times 10^{-10}$ |

Example 6 Construction of Expression Vector of Fusion Protein D1-D3

TABLE 5

| Code of fusion protein | Partial sequence of GLP-1 receptor agonist | Mutation site of FGF21 variant | Fusion protein SEQ ID NO: |
|---|---|---|---|
| D1 | SEQ ID NO: 15 | 98R, 167H, 171A | 16 |
| D2 | SEQ ID NO: 15 | 98R, 167H, 171A, 175L | 17 |
| D3 | SEQ ID NO: 15 | 98R, 167H, 171G, 175L | 18 |

Firstly, the upstream fragment (including part of GLP-1) and the downstream fragment (Fc-FGF21) were obtained by PCR amplification. The PCR amplification procedure was as follows: pre-denaturation at 98° C. for 5 min; denaturation at 98° C. for 10 s; annealing at 56° C. for 10 s; extending at 72° C. for 5s or 10 s; repeating 30 cycles; and extending at 72° C. for 8 min. The PCR product was then detected by 1.0% agarose gel electrophoresis and the upstream and downstream fragments were recovered by using an OMEGA gel recovery kit. The obtained upstream fragment and downstream fragment were subjected to full-length sequence by SOE PCR. The SOE PCR amplification procedure was as follows: pre-denaturation at 98° C. for 5 min; denaturation at 98° C. for 10 s; annealing at 56° C. for 10 s; extending at 72° C. for 15s; repeating 30 cycles; and extending at 72° C. for 8 min. Then the full-length target gene was recovered by Gel Extraction Kit kit (OMEGA, America).

The sequence of the objective gene and the vector plasmid pcDNA3.4 were digested with the endonuclease HindIII and EcoRI (TAKARA, Japan) at 37° C., and the digested product was purified and recovered by using a Gel Extraction Kit according to the manufacturer's instructions. The purified objective gene was ligated with the vector using a DNA Ligation Kit Ver.2.1 (TAKARA, Japan) according to the manufacturer's instructions and incubated at 16° C. for 1 hour to obtain a recombinant expression plasmid.

The above recombinant expression plasmid was transformed into competent cells DH5a, and bacteria was coated into an ampicillin plate. The monoclonal on the plate was picked and cultured in 1 ml of LB medium (peptone 10 g/L, yeast extract 5 g/L, sodium chloride 10 g/L and agar 2%, antibiotic content 100 μg/mL) to extract the plasmid. After sequencing and validation, a series of validated correct expression vectors were extracted with Invitrogen Plasmid Kit and digested with restriction enzyme PvuI (TAKARA, Japan). After linearization, the product was purified and recovered by ethanol precipitation method and stored at −20° C. for future use.

The primers used in the experiment are as follows:

```
Amplification primers of the upstream fragment (containing the GLP-1 portion)
Primer AUZ-F:
                                                          (SEQ ID NO: 29)
cccaagcttgccgccaccatgaccagactgaccgtgc Primer lfc1-R:
                                                          (SEQ ID NO: 30)
gccgtacttgctctcagatccaccgcctccgcttc Amplification primers of the downstream fragment (Fc-FGF21):
Primer lfc1-F:
                                                          (SEQ ID NO: 31)
gcggaggcggtggatctgagagcaagtacggcccc Primer fgf21-R:
                                                          (SEQ ID NO: 32)
ccggaattctcatcagctggcgtagctagggct SOE PCR primers:
Primer AUZ-F:
                                                          (SEQ ID NO: 29)
cccaagcttgccgccaccatgaccagactgaccgtgc Primer fgf21-R:
                                                          (SEQ ID NO: 32)
ccggaattctcatcagctggcgtagctagggct
```

Example 7 Expression of Fusion Protein D1-D3

HEK293F host cells (Invitrogen, Freestyle 293F) were resuscitated with 293 Expression Medium. The host cells were transfected when the cell density was about 1\ $10^6$ cells/mL. About $3 \times 10^7$ cells were transfected, and the linearized expression vector prepared in Example 6 was about 30 μg. The cells were transfected with Expi Fectamine 293 Reagent Transfection Kit. After transfection, the cells were cultured in 30 mL of 293 Expression Medium. On the second day of culture, transformants were started to be screened with geneticin G418 (merck). The medium was replaced every 3 days depending on the growth of the cells. After about 14 days of selection, resistant clones appeared and could be expanded. The cell passage density was about $0.5 \times 10^6$ cells/mL. The obtained mixed clone was subcultured with 293 Expression Medium. When the cell viability was about 90%, the cell culture fluid was collected.

Example 8 Purification of Fusion Protein D1-D3

The cell culture solution prepared in Example 7 was centrifuged at 200 g for 10 min, and the supernatant was centrifuged at 8000 rpm for 30 min, and the supernatant was collected. The collected cell culture supernatant was subjected to affinity purification by Protein A chromatography (EzFast Protein A Diamond, Bestchrom). The equilibration solution was 20 mM PBS, 0.15 M NaCl, pH 7.4. The eluent was 0.1 M glycine of pH 3.2. The target eluate was collected at target absorption peak and dialyzed with PBS buffer to take part of the sample for mass spectrometry. Mass spectrometry detection molecular weight was consistent with theoretical molecular weight, and they were in homodimeric form. At the same time, the collected samples were detected by 10% SDS-PAGE electrophoresis after reduction and non-reduction. The fusion protein S2 is taken as an example, and the purification result thereof is shown in FIG. 12. The first band is a protein molecular weight marker, the second band is fermentation supernatant of the fusion protein D2, the third band is the purified fusion protein D2, and the fourth band is the reduced fusion protein D2.

Figure 5:
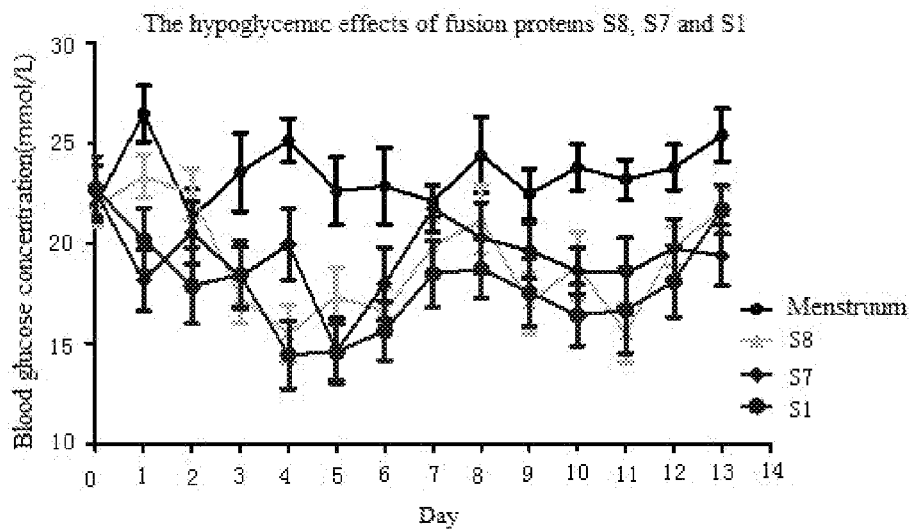
FIG. 5 shows the hypoglycemic effects of the fusion proteins S8, S7 and 51 of the present application.

Example 9 A Study of the Hypoglycemic and Liver-Protecting Efficacy of Fusion Protein S1/S7/S8 in db/db Mouse Model The efficacy of the fusion protein in the db/db mouse model (Model Animal Institute of Nanjing University) was studied. During the experiment, the purified fusion protein was diluted with 10 mM PBS. The db/db mice were randomly divided into four groups, including solvent group, S7 group (SEQ ID NO: 26), 51 group (SEQ ID NO: 9), and S8 group (SEQ ID NO: 27). Each db/db mice was injected with 40 nM/kg of corresponding fusion protein. The dosage volume was 10 ml/kg. Each fusion protein was injected to nine mice which were administered once a week for two weeks. The changes of blood sugar were observed after administration (results shown in FIG. 5). Compared with S8 group, on the first day and the second day after administration, 51 group showed a rapid hypoglycemic effect while 51 group showed a more stable hypoglycemic effect. Compared with S7 group, 51 group had a better hypoglycemic effect.

Figure 6:
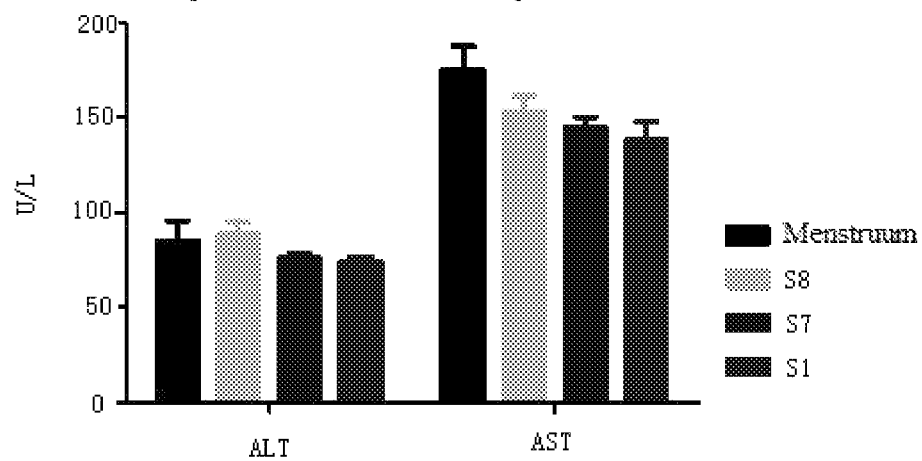
FIG. 6 shows the protective effects of the fusion proteins S8, S7 and 51 of the present application on the liver.

Two weeks after administration, the mice were sacrificed and their blood levels of aspartate aminotransferase (AST) and alanine aminotransferase (ALT) were measured (results shown in FIG. 6) to evaluate the protective effect of the drug on liver function. The data showed that S7 group and 51 group significantly reduced the levels of aspartate aminotransferase (AST) and alanine aminotransferase (ALT), indicating a protective effect on the liver.

It can be seen that 51 group showed better effects than S7 group on reducing blood sugar and protecting liver.

Figure 7:
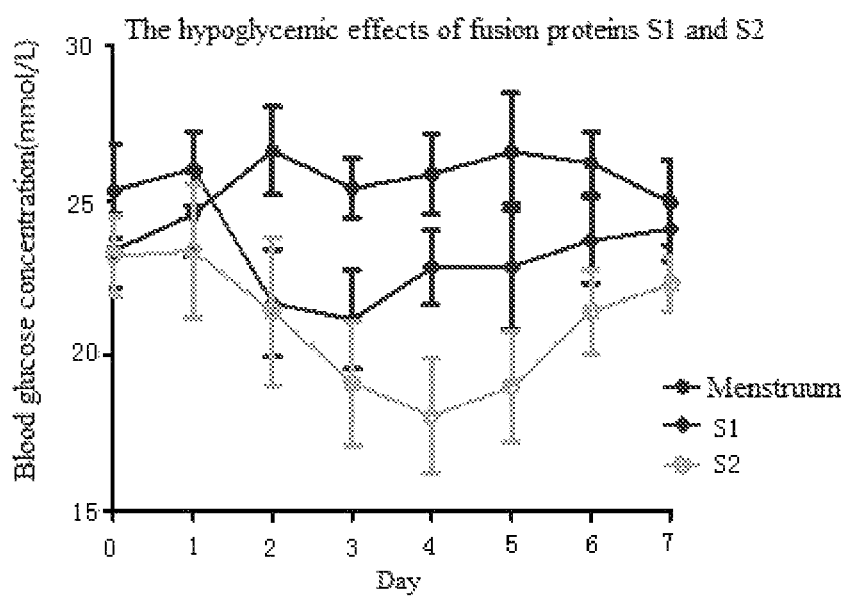
FIG. 7 shows the hypoglycemic effects of the fusion proteins S1 and S2 of the present application.

Example 10 A Study of the Single Hypoglycemic Efficacy of Fusion Protein S1/S2 in db/db Mouse Model The db/db model mice (Model Animal Institute of Nanjing University) were randomly divided into 3 groups, including the vehicle group, 51 group (SEQ ID NO: 9), and S2 group (SEQ ID NO: 10). Each db/db mice was injected with 40 nM/kg of corresponding fusion protein. The dosage volume was 10 ml/kg. Each fusion protein was injected to nine mice and administered once. The changes of blood sugar were observed after administration (results shown in FIG. 7). As seen in FIG. 7, it was found that both S1 group and S2 group can significantly reduce blood glucose compared with the vehicle group, and S2 group showed a relatively better hypoglycemic effect.

Figure 8:
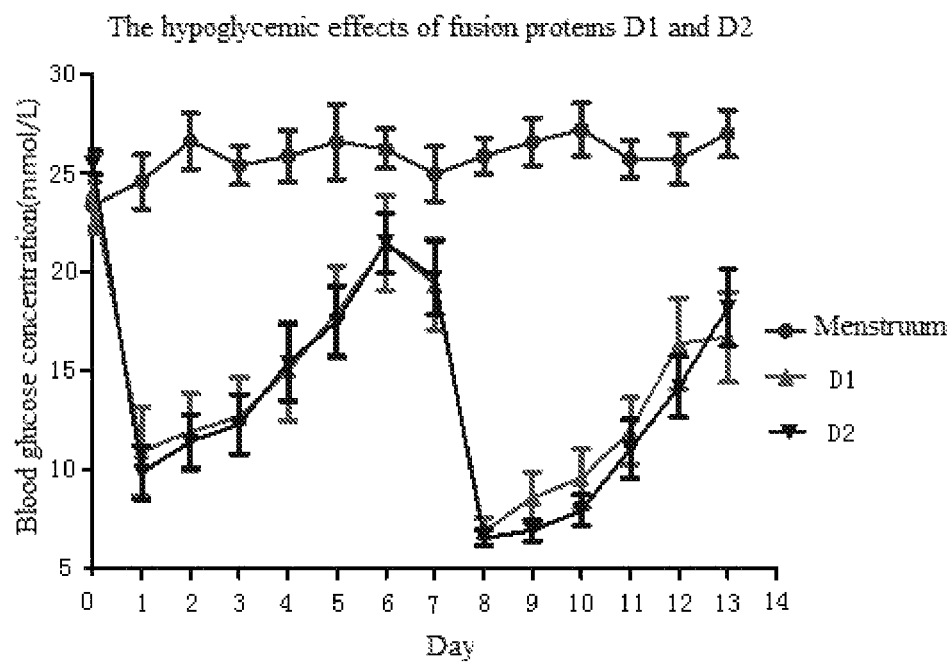
FIG. 8 shows the hypoglycemic effects of the fusion proteins D1 and D2 of the present application.

Example 11 A Study of the Hypoglycemic and Lipid-Lowering Efficacy of Fusion Protein D1/D2 in db/db Mouse Model The db/db model mice (Model Animal Institute of Nanjing University) were randomly divided into 4 groups, including the vehicle group, D1 group (SEQ ID NO: 16), and D2 group (SEQ ID NO: 17). Each db/db mice was injected with 30 nM/kg of corresponding fusion protein. The dosage volume was 10 ml/kg. Each fusion protein was injected to nine mice which were administered once a week for two weeks. The changes of blood sugar were observed after administration (results shown in FIG. 8). As seen in FIG. 8, both fusion proteins D1 and D2 showed strong hypoglycemic ability.

Figure 9:
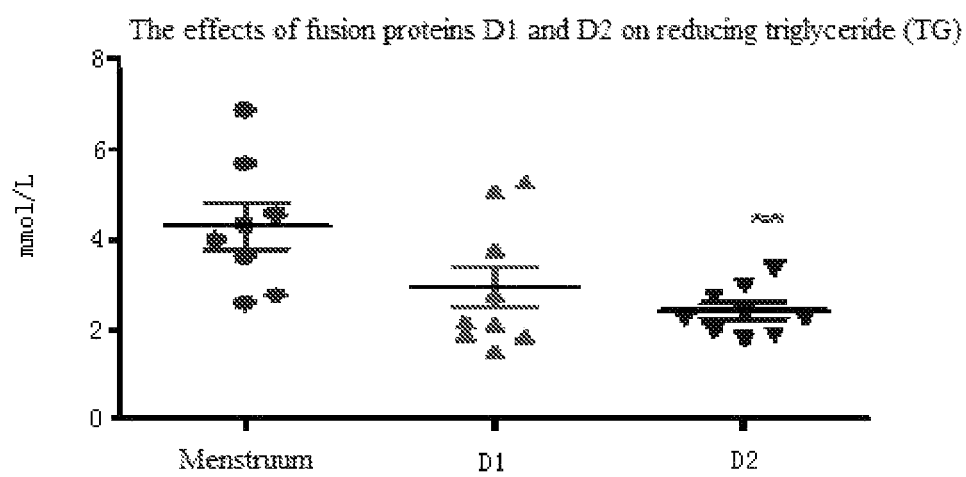
FIG. 9 shows the effects of the fusion proteins D1 and D2 of the present application on reducing triglyceride (TG).
Figure 10:
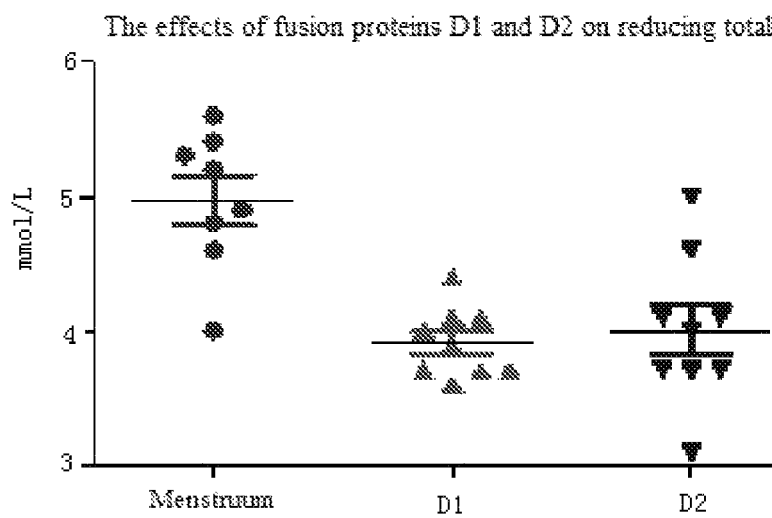
FIG. 10 shows the effects of the fusion proteins D1 and D2 of the present application on reducing total cholesterol.

Fourteen days after initial administration, the results of serum triglyceride (TG) are shown in FIG. 9 and the results of total cholesterol (TCHO) are shown in FIG. 10. The results showed that fusion protein D1 and D2 had significant effects on reducing triglycerides and total cholesterol.

Figure 11:
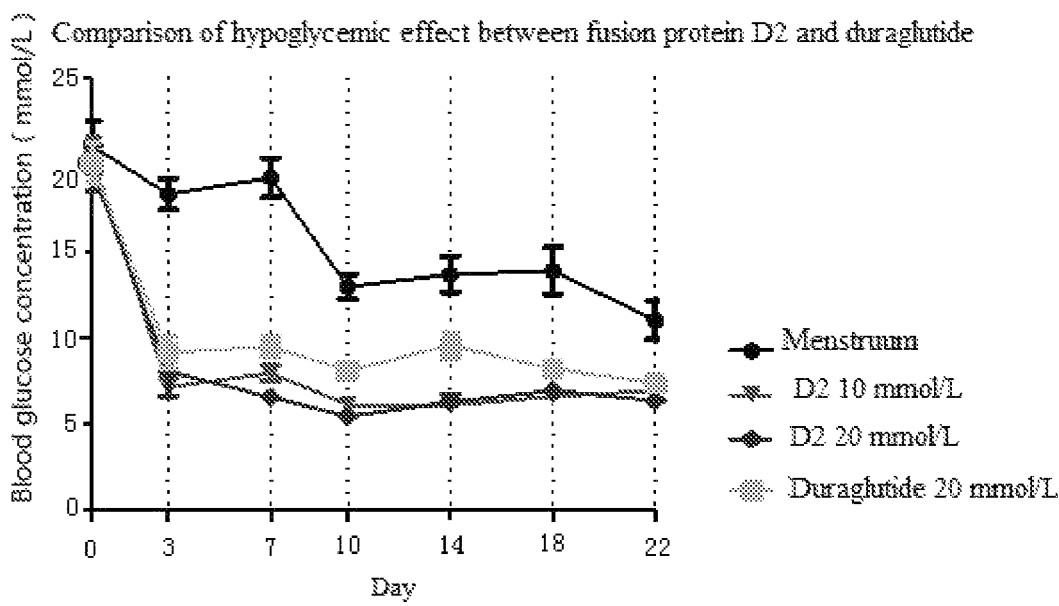
FIG. 11 shows the hypoglycemic effects of the fusion proteins D2 of the present application.

Example 12 A Study of the Hypoglycemic Efficacy of Fusion Protein D2 and Duraglutide in Ob/ob Mouse Model The efficacy of the fusion protein in the ob/ob mouse model (Model Animal Institute of Nanjing University) was studied. During the experiment, the purified fusion protein was diluted with 10 mM PBS. The mice were randomly divided into 4 groups, including the vehicle group, D2 group (SEQ ID NO: 17) with 10 nmol/kg, and D2 group (SEQ ID NO: 17) with 20 nmol/kg, the Duraglutide group (Lily) with 20 nmol/kg. The dosage volume was 10 ml/kg. Each fusion protein was injected to nine mice which were administered twice a week for 3 weeks. Samples were taken before each administration to detect changes of blood sugar. The results are shown in FIG. 11. The results showed that the fusion protein D2 had a better hypoglycemic effect and a more stable hypoglycemic curve than duraglutide.

Example 13 Construction of Expression Vector Plasmid-X1

The objective gene was synthesized by Suzhou Genewiz Biological Technology Co., Ltd. The sequence of the objective gene is shown in Table 3. The sequence of the objective gene and the vector plasmid pcDNA3.4 were digested with the endonuclease HindIII and EcoRI (TAKARA, Japan) at 37° C., and the digested product was purified and recovered by using a Gel Extraction Kit according to the manufacturer's instructions. The purified objective gene was ligated with the vector using a DNA Ligation Kit Ver.2.1 (TAKARA, Japan) according to the manufacturer's instructions and incubated at 16° C. for 1 hour to obtain a recombinant expression plasmid.

The above recombinant expression plasmid was transformed into competent cells DH5a, and bacteria was coated into an ampicillin plate. The monoclonal on the plate was picked and cultured in 1 ml of LB medium (peptone 10 g/L, yeast extract 5 g/L, sodium chloride 10 g/L and agar 2%, antibiotic content 100 μg/mL) to extract the plasmid. After sequencing and validation by Guangzhou Aiji Biotechnology Co., Ltd., a series of validated correct expression vectors were extracted with Invitrogen Plasmid Kit and digested with restriction enzyme PvuI (TAKARA, Japan). After linearization, the product was purified and recovered by ethanol precipitation method and stored at −20° C. for future use.

TABLE 6

| The name of the fusion protein encoded by the objective gene | Amino acid sequence of fusion protein |
| --- | --- |
| D3 | SEQ ID NO: 18 |
| S3 | SEQ ID NO: 11 |
| FGF21 mutant control fusion protein SPC | SEQ ID NO: 33 |
| S2 | SEQ ID NO: 10 |

Example 14 Transfection of Fusion Protein Expression Vectors and Expression in Cells HEK293F host cells (Invitrogen, Freestyle 293F) were resuscitated with 293 Expi Medium. The host cells were transfected when cell density was about $1 \times 10^6$ cells/mL. About $3 \times 10^7$ cells were transfected, and the linearized expression vector prepared in Example 13 was about 30 μg. The cells were transfected with Expi Fectamine293 Reagent Transfection Kit. After transfection, the cells were cultured in 30 mL of 293 Expression Medium. On the second day of culture, transformants were started to be screened with geneticin G418 (Merck). The medium was replaced every 3 days depending on the growth of the cells. After about 14 days of selection, resistant clones appeared and could be expanded. The cell passage density was about $0.5 \times 10^6$ cells/mL. The obtained mixed clone was subcultured with 293 Expression Medium. When the cell viability was about 90%, the cell culture fluid was collected.

Figure 13:
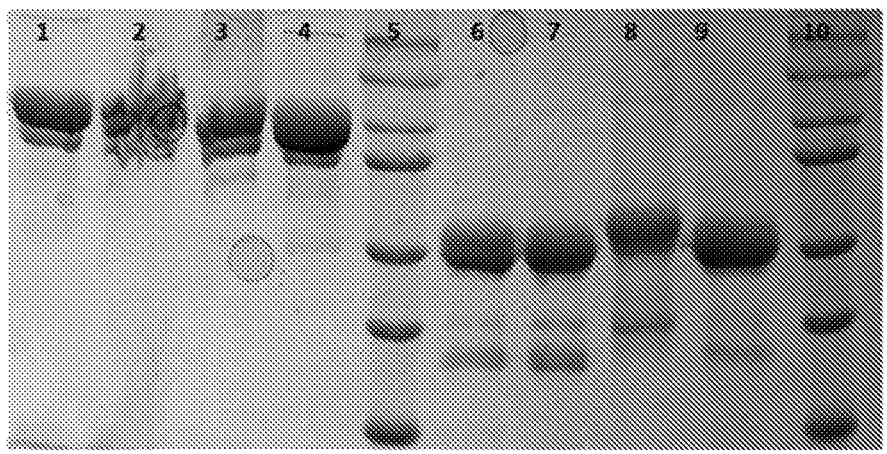
FIG. 13 shows the results of purification of the fusion proteins S2, D3 and D2 of the present application.

Example 15 Purification of Fusion Protein from the Collected Cell Fermentation Broth The cell culture solution prepared in Example 14 was centrifuged at 200 g for 10 min, and the supernatant was centrifuged at 8000 rpm for 30 min, and the supernatant was collected. The collected cell culture supernatant was subjected to affinity purification by Protein A chromatography (EzFast Protein A Diamond, Bestchrom). The equilibration solution was 20 mM PBS, 0.15 M NaCl, pH 7.4. The eluent was 0.1 M glycine of pH 3.2. The target eluate was collected at target absorption peak and dialyzed with PBS buffer to take part of the sample for mass spectrometry. Mass spectrometry (Accurate-Mass Q-TOF LC/MS, Type G6530, Agilent Technologies) detection molecular weight was consistent with theoretical molecular weight, and they were in homodimeric form. At the same time, the collected samples were detected by 10% SDS-PAGE electrophoresis after reduction and non-reduction. The results are shown in FIG. 13. Bands 1 to 10 in FIG. 13 are sequentially SPC, S3, D3, S2, Marker, SPC processed by DTT, S3 processed by DTT, D3 processed by DTT, S2 processed by DTT and Marker.

Figure 14:
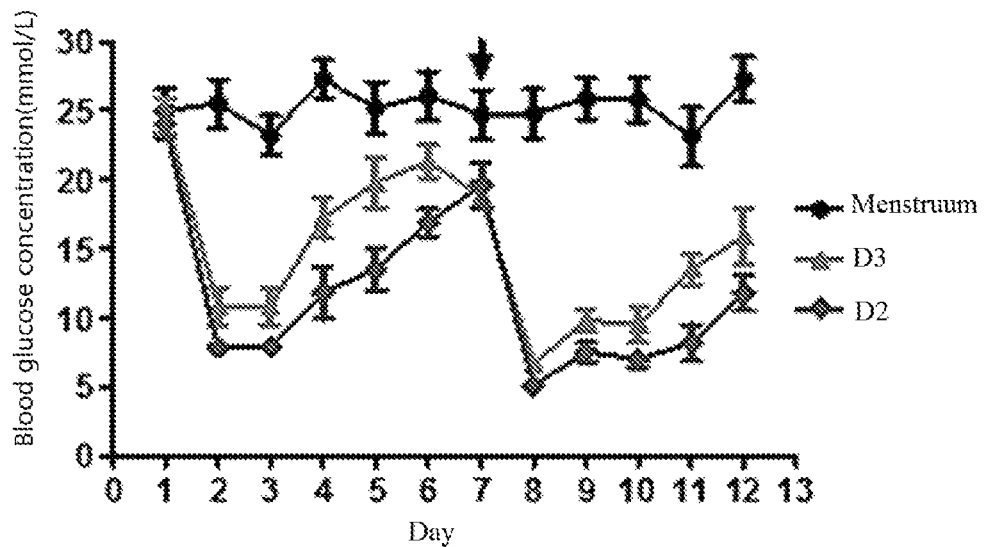
FIG. 14 shows the hypoglycemic effects of the fusion proteins D3 and D2 of the present application.

Example 16 A Study of the Hypoglycemic and Lipid-Improving Effects of Fusion Protein in db/db Mouse Model The efficacy of fusion proteins D3 and D2 in the db/db mouse model (Jiangsu GemPharmatech Co., Ltd.) was studied. During the experiment, the purified fusion protein was diluted with 10 mM PBS. The db/db mice that meet the experimental requirements were randomly divided into three groups, including solvent group, the fusion protein D3 group and D2 group. Each db/db mice was injected with 10 nM/kg of corresponding fusion protein. The dosage volume was 10 ml/kg. Each fusion protein was injected to nine mice which were administered once a week for two weeks. The changes of blood sugar, body weight, and food intake were observed after administration (results shown in FIG. 14). Compared with the vehicle control group, it has hypoglycemic activity.

Figure 15:
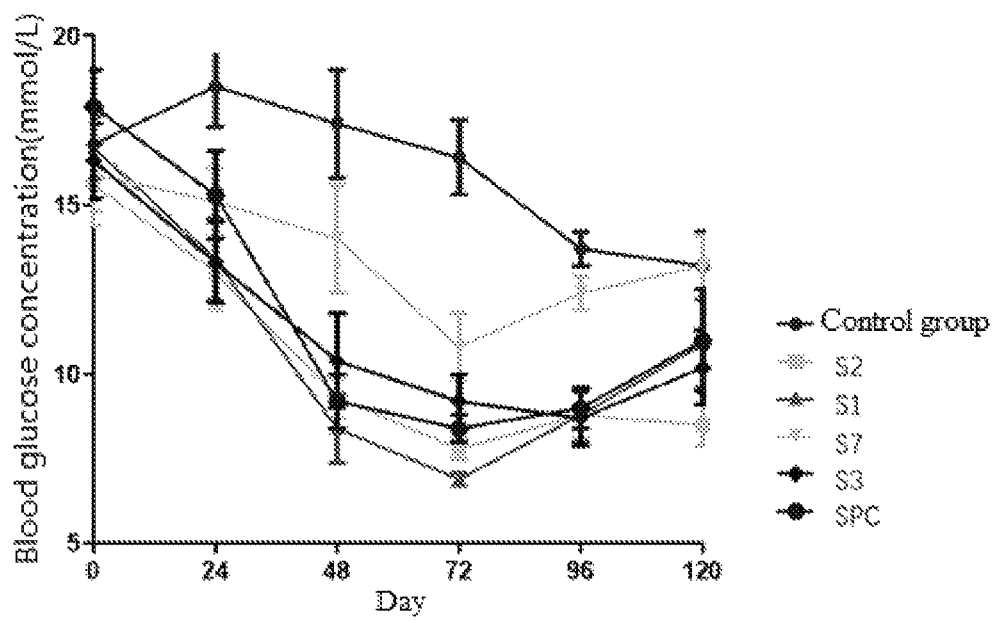
FIG. 15 shows the hypoglycemic effects of the fusion proteins S2, S1, S7 and S3 of the present application.

Example 17 A Study of the Hypoglycemic and Lipid-Improving Efficacy of Fusion Protein in ob/ob Mouse Model The efficacy of fusion proteins in the ob/ob mouse model (Jiangsu GemPharmatech Co., Ltd.) was studied. During the experiment, the purified fusion protein was diluted with 10 mM PBS. The db/db mice that meet the experimental requirements were randomly divided into six groups, including the control group (PBS buffer only), S2, S1, S7, S3 and SPC. Each db/db mice was injected with 20 nM/kg of corresponding fusion protein. The dosage volume was 10 ml/kg. Each fusion protein was injected to eight mice and administered once. The changes of blood sugar, body weight, and food intake were observed after administration (results shown in FIG. 15). Compared with the control group, S1, S2 and S3 showed a weak hypoglycemic effect at 24 h after administration; S1, S2, S3 and SPC showed a strong hypoglycemic effect at 48 h after administration ($P<0.001$, $P<0.05$), wherein the hypoglycemic effect of S2 was maintained at 120 h ($P<0.01$, $P<0.001$), while the others were only maintained until 96 h after administration, and S1 was slightly superior in the hypoglycemic range. S7 showed no significant hypoglycemic effect at other times except that it showed strong hypoglycemic effect at 72 h.

The foregoing detailed description is provided by way of explanation and illustration, and is not intended to limit the scope of the appended claims. Various changes in the implementation methods enumerated in the present application are obvious to those skilled in the art and are also within the scope of the appended claims and their equivalent schemes.

What is claimed is:

1. An amino acid sequence of a FGF21 variant that includes amino acid substitutions compared to the amino acid sequence shown in SEQ ID NO: 1, the amino acid substitutions comprising:
   an amino acid substitution at position 98, wherein the amino acid substitution at position 98 is L98R,
   an amino acid substitution at position 167, wherein the amino acid substitution at position 167 is S167H,
   an amino acid substitution at position 171, wherein the amino acid substitution at position 171 is P171A, and
   an amino acid substitution at position 175, wherein the amino acid substitution at position 175 is selected from the group consisting of R175L, R175P and R175H.

2. The FGF21 variant of claim 1, wherein the amino acid substitutions compared to the amino acid sequence shown in SEQ ID NO: 1 comprise amino acid substitutions selected from any one of the following combinations of amino acid substitutions:
   L98R, S167H, P171A and R175L; and,
   L98R, G113R, L114Q, R135C, S167H, P171A and R175L.

3. The FGF21 variant of claim 1, which comprises the amino acid sequence of any one of SEQ ID NOs: 3, 35, 36 and 37.

4. A fusion protein comprising the FGF21 variant of claim 1.

5. The fusion protein of claim 4, which further comprises an IgG constant region domain or a fragment thereof.

6. The fusion protein of claim 5, wherein the IgG constant region domain comprises the amino acid sequence of any one of SEQ ID NO: 5-6.

7. The fusion protein of claim 5, wherein the N-terminus of the FGF21 variant is directly or indirectly linked to the C-terminus of the IgG constant region domain or the fragment thereof.

8. The fusion protein of claim 4, which comprises the amino acid sequence of any one of SEQ ID NOs: 10 and 12-14.

9. The fusion protein of claim 4, which further comprises a GLP-1 receptor agonist portion.

10. The fusion protein of claim 9, wherein the GLP-1 receptor agonist portion comprises the amino acid sequence of any one of SEQ ID NO: 15 and SEQ ID NO: 28.

11. The fusion protein of claim 9, which comprises the amino acid sequence of SEQ ID NO: 17.

12. The fusion protein of claim 4, which further comprises:
   an IgG constant region domain or a fragment thereof, and
   a GLP-1 receptor agonist portion, wherein the C-terminus of the GLP-1 receptor agonist portion is directly or indirectly linked to the N-terminus of the IgG constant region domain or the fragment thereof.

13. The fusion protein of claim 4, which further comprises:
    an IgG constant region domain or a fragment thereof,
    a GLP-1 receptor agonist portion,
    wherein the N-terminus of the FGF21 variant is directly or indirectly linked to the C-terminus of the IgG constant region domain or the fragment thereof.

14. A protein multimer comprising two or more fusion proteins of claim 4.

15. The protein multimer of claim 14, which is a homodimer.

16. A pharmaceutical composition comprising:
    the FGF21 variant of claim 1, a fusion protein comprising the FGF21 variant, or a protein multimer comprising two or more of the fusion proteins, and
    optionally one or more pharmaceutically acceptable carriers.

17. A method of treating a metabolic disease in a patient in need thereof, the method comprising:
    administering a therapeutically effective amount of the FGF21 variant of claim 1 to the patient.

18. The method of claim 17, wherein the metabolic disease is selected from the group consisting of diabetes, obesity and hepatic steatosis.

19. The FGF21 variant of claim 1, wherein the amino acid substitutions compared to the amino acid sequence shown in SEQ ID NO: 1 comprise L98R, S167H, P171A and R175L.

* * * * *

SEQUENCE LISTING

```
<160> NUMBER OF SEQ ID NOS: 37

<210> SEQ ID NO 1
<211> LENGTH: 181
<212> TYPE: PRT
<213> ORGANISM: Homo sapiens

<400> SEQUENCE: 1

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

```
<210> SEQ ID NO 2
<211> LENGTH: 181
<212> TYPE: PRT
<213> ORGANISM: Artificial Sequence
<220> FEATURE:
<223> OTHER INFORMATION: FGF21 variant
<220> FEATURE:
<221> NAME/KEY: UNSURE
<222> LOCATION: (98)..(98)
<223> OTHER INFORMATION: Xaa at position 98 is Leu, Arg, Asp, Glu or Lys
<220> FEATURE:
<221> NAME/KEY: UNSURE
<222> LOCATION: (113)..(114)
<223> OTHER INFORMATION: Xaa at position 113 is Gly or Arg; Xaa at
      position 114 is Leu or Gln
<220> FEATURE:
<221> NAME/KEY: UNSURE
<222> LOCATION: (135)..(135)
<223> OTHER INFORMATION: Xaa at position 135 is Arg or Cys
<220> FEATURE:
<221> NAME/KEY: UNSURE
<222> LOCATION: (167)..(167)
<223> OTHER INFORMATION: Xaa at position 167 is Ser, Cys, Arg or His
<220> FEATURE:
<221> NAME/KEY: UNSURE
<222> LOCATION: (171)..(171)
<223> OTHER INFORMATION: Xaa at position 171 is Pro, Cys, Gly or Ala
<220> FEATURE:
<221> NAME/KEY: UNSURE
<222> LOCATION: (175)..(175)
<223> OTHER INFORMATION: Xaa at position 175 is Arg, His, Pro or Leu

<400> SEQUENCE: 2

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Xaa Leu Leu Glu Asp Gly Tyr Asn Val Tyr Gln Ser Glu Ala His
            100                 105                 110

Xaa Xaa Pro Leu His Leu Pro Gly Asn Lys Ser Pro His Arg Asp Pro
        115                 120                 125

Ala Pro Arg Gly Pro Ala Xaa Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Xaa Met Val Gly Xaa Ser Gln Gly Xaa Ser
                165                 170                 175

Pro Ser Tyr Ala Ser
            180

<210> SEQ ID NO 3
<211> LENGTH: 181
<212> TYPE: PRT
<213> ORGANISM: Artificial Sequence
<220> FEATURE:
<223> OTHER INFORMATION: FGF21 98R171A167H175L

<400> SEQUENCE: 3
```

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Arg Leu Leu Glu Asp Gly Tyr Asn Val Tyr Gln Ser Glu Ala His
                    100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu His Met Val Gly Ala Ser Gln Gly Leu Ser
                165                 170                 175

Pro Ser Tyr Ala Ser
            180

<210> SEQ ID NO 4
<211> LENGTH: 181
<212> TYPE: PRT
<213> ORGANISM: Artificial Sequence
<220> FEATURE:
<223> OTHER INFORMATION: FGF21 98R171G167H175L

<400> SEQUENCE: 4

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Arg Leu Leu Glu Asp Gly Tyr Asn Val Tyr Gln Ser Glu Ala His
                    100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu His Met Val Gly Ser Gln Gly Leu Ser
                165                 170                 175

<210> SEQ ID NO 5
<211> LENGTH: 228
<212> TYPE: PRT
<213> ORGANISM: Artificial Sequence
<220> FEATURE:
<223> OTHER INFORMATION: fc lily

<400> SEQUENCE: 5

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225
```

<210> SEQ ID NO 6
<211> LENGTH: 228
<212> TYPE: PRT
<213> ORGANISM: Artificial Sequence
<220> FEATURE:
<223> OTHER INFORMATION: IgG4 Fc hec

<400> SEQUENCE: 6

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
```

```
                  50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 7
<211> LENGTH: 15
<212> TYPE: PRT
<213> ORGANISM: Artificial Sequence
<220> FEATURE:
<223> OTHER INFORMATION: linker

<400> SEQUENCE: 7

Gly Gly Gly Gly Ser Gly Gly Gly Gly Ser Gly Gly Gly Gly Ser
1               5                  10                  15

<210> SEQ ID NO 8
<211> LENGTH: 16
<212> TYPE: PRT
<213> ORGANISM: Artificial Sequence
<220> FEATURE:
<223> OTHER INFORMATION: linker a

<400> SEQUENCE: 8

Gly Gly Gly Gly Ser Gly Gly Gly Gly Ser Gly Gly Gly Gly Ser Ala
1               5                  10                  15

<210> SEQ ID NO 9
<211> LENGTH: 424
<212> TYPE: PRT
<213> ORGANISM: Artificial Sequence
<220> FEATURE:
<223> OTHER INFORMATION: Fusion Protein S1 98R167H171A

<400> SEQUENCE: 9

Glu Ser L

```
Ser Gln Glu Asp Pro Glu Val Gln Phe Asn Trp Tyr Val Asp Gly Val
 50                  55                  60

Glu Val His Asn Ala Lys Thr Lys Pro Arg Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Gly Gly Gly Ser Gly Gly Gly Ser Gly Gly
225                 230                 235                 240

Gly Gly Ser His Pro Ile Pro Asp Ser Ser Pro Leu Leu Gln Phe Gly
                245                 250                 255

Gly Gln Val Arg Gln Arg Tyr Leu Tyr Thr Asp Asp Ala Gln Gln Thr
            260                 265                 270

Glu Ala His Leu Glu Ile Arg Glu Asp Gly Thr Val Gly Gly Ala Ala
        275                 280                 285

Asp Gln Ser Pro Glu Ser Leu Leu Gln Leu Lys Ala Leu Lys Pro Gly
    290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Arg Leu Leu Glu Asp Gly Tyr Asn Val Tyr Gln Ser
            340                 345                 350

Glu Ala His Gly Leu Pro Leu His Leu Pro Gly Asn Lys Ser Pro His
        355                 360                 365

Arg Asp Pro Ala Pro Arg Gly Pro Ala Arg Phe Leu Pro Leu Pro Gly
    370                 375                 380

Leu Pro Pro Ala Leu Pro Glu Pro Pro Gly Ile Leu Ala Pro Gln Pro
385                 390                 395                 400

Pro Asp Val Gly Ser Ser Asp Pro Leu His Met Val Gly Ala Ser Gln
                405                 410                 415

Gly Arg Ser Pro Ser Tyr Ala Ser
            420

<210> SEQ ID NO 10
<211> LENGTH: 424
<212> TYPE: PRT
<213> ORGANISM: Artificial Sequence
<220> FEATURE:
```

<223> OTHER INFORMATION: Fusion Protein S2 98R171A167H175L

<400> SEQUENCE: 10

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys L

```
Pro Asp Val Gly Ser Ser Asp Pro Leu His Met Val Gly Ala Ser Gln
                405                 410                 415

Gly Leu Ser Pro Ser Tyr Ala Ser
            420
```

<210> SEQ ID NO 11
<211> LENGTH: 424
<212> TYPE: PRT
<213> ORGANISM: Artificial Sequence
<220> FEATURE:
<223> OTHER INFORMATION: Fusion Protein S3 98R171G167H175L

<400> SEQUENCE: 11

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Ser Gly Gly Gly Gly Ser Gly Gly Gly
225                 230                 235                 240

Gly Gly Ser His Pro Ile Pro Asp Ser Ser Pro Leu Leu Gln Phe Gly
                245                 250                 255

Gly Gln Val Arg Gln Arg Tyr Leu Tyr Thr Asp Asp Ala Gln Gln Thr
            260                 265                 270

Glu Ala His Leu Glu Ile Arg Glu Asp Gly Thr Val Gly Gly Ala Ala
        275                 280                 285

Asp Gln Ser Pro Glu Ser Leu Leu Gln Leu Lys Ala Leu Lys Pro Gly
    290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335
```

```
Ser Phe Arg Glu Arg Leu Leu Glu Asp Gly Tyr Asn Val Tyr Gln Ser
                340                 345                 350

Glu Ala His Gly Leu Pro Leu His Leu Pro Gly Asn Lys Ser Pro His
            355                 360                 365

Arg Asp Pro Ala Pro Arg Gly Pro Ala Arg Phe Leu Pro Leu Pro Gly
        370                 375                 380

Leu Pro Pro Ala Leu Pro Glu Pro Pro Gly Ile Leu Ala Pro Gln Pro
385                 390                 395                 400

Pro Asp Val Gly Ser Ser Asp Pro Leu His Met Val Gly Gly Ser Gln
                405                 410                 415

Gly Leu Ser Pro Ser Tyr Ala Ser
            420

<210> SEQ ID NO 12
<211> LENGTH: 424
<212> TYPE: PRT
<213> ORGANISM: Artificial Sequence
<220> FEATURE:
<223> OTHER INFORMATION: Fusion Protein S4 98R171A167H175P

<400> SEQUENCE: 12

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Ser Gly Gly Gly Gly Ser Gly Gly Gly Gly
225                 230                 235                 240

Gly Gly Ser His Pro Ile Pro Asp Ser Ser Pro Leu Leu Gln Phe Gly
                245                 250                 255

Gly Gln Val Arg Gln Arg Tyr Leu Tyr Thr Asp Asp Ala Gln Gln Thr
            260                 265                 270
```

```
Glu Ala His Leu Glu Ile Arg Glu Asp Gly Thr Val Gly Gly Ala Ala
            275                 280                 285

Asp Gln Ser Pro Glu Ser Leu Leu Gln Leu Lys Ala Leu Lys Pro Gly
    290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Arg Leu Leu Glu Asp Gly Tyr Asn Val Tyr Gln Ser
            340                 345                 350

Glu Ala His Gly Leu Pro Leu His Leu Pro Gly Asn Lys Ser Pro His
        355                 360                 365

Arg Asp Pro Ala Pro Arg Gly Pro Ala Arg Phe Leu Pro Leu Pro Gly
    370                 375                 380

Leu Pro Pro Ala Leu Pro Glu Pro Pro Gly Ile Leu Ala Pro Gln Pro
385                 390                 395                 400

Pro Asp Val Gly Ser Ser Asp Pro Leu His Met Val Gly Ala Ser Gln
                405                 410                 415

Gly Pro Ser Pro Ser Tyr Ala Ser
            420

<210> SEQ ID NO 13
<211> LENGTH: 424
<212> TYPE: PRT
<213> ORGANISM: Artificial Sequence
<220> FEATURE:
<223> OTHER INFORMATION: Fusion Protein S5 98R171A167H175H

<400> SEQUENCE: 13

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
        195                 200                 205
```

Val Met His Glu Ala Leu His Asn His Tyr Thr Gln Lys Ser Leu Ser
210                 215                 220

Leu Ser Leu Gly Gly Gly Gly Ser Gly Gly Gly Gly Ser Gly Gly
225                 230                 235                 240

Gly Gly Ser His Pro Ile Pro Asp Ser Ser Pro Leu Leu Gln Phe Gly
                245                 250                 255

Gly Gln Val Arg Gln Arg Tyr Leu Tyr Thr Asp Asp Ala Gln Gln Thr
            260                 265                 270

Glu Ala His Leu Glu Ile Arg Glu Asp Gly Thr Val Gly Gly Ala Ala
                275                 280                 285

Asp Gln Ser Pro Glu Ser Leu Leu Gln Leu Lys Ala Leu Lys Pro Gly
290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Arg Leu Leu Glu Asp Gly Tyr Asn Val Tyr Gln Ser
                340                 345                 350

Glu Ala His Gly Leu Pro Leu His Leu Pro Gly Asn Lys Ser Pro His
                355                 360                 365

Arg Asp Pro Ala Pro Arg Gly Pro Ala Arg Phe Leu Pro Leu Pro Gly
370                 375                 380

Leu Pro Pro Ala Leu Pro Glu Pro Pro Gly Ile Leu Ala Pro Gln Pro
385                 390                 395                 400

Pro Asp Val Gly Ser Ser Asp Pro Leu His Met Val Gly Ala Ser Gln
                405                 410                 415

Gly His Ser Pro Ser Tyr Ala Ser
                420

<210> SEQ ID NO 14
<211> LENGTH: 424
<212> TYPE: PRT
<213> ORGANISM: Artificial Sequence
<220> FEATURE:
<223> OTHER INFORMATION: Fusion Protein S6 98R171A167H175P113R114Q135C

<400> SEQUENCE: 14

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Lys Pro Lys Asp Thr
            20                  25                  30

Leu Met Ile Ser Arg Thr Pro Glu Val Thr Cys Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

| Val | Ser | Leu | Thr | Cys | Leu | Val | Lys | Gly | Phe | Tyr | Pro | Ser | Asp | Ile | Ala |
| 145 | | | | 150 | | | | | 155 | | | | | 160 | |

| Val | Glu | Trp | Glu | Ser | Asn | Gly | Gln | Pro | Glu | Asn | Asn | Tyr | Lys | Thr | Thr |
| | | | 165 | | | | | 170 | | | | | 175 | | |

| Pro | Pro | Val | Leu | Asp | Ser | Asp | Gly | Ser | Phe | Phe | Leu | Tyr | Ser | Lys | Leu |
| | | | 180 | | | | | 185 | | | | | 190 | | |

| Thr | Val | Asp | Lys | Ser | Arg | Trp | Gln | Glu | Gly | Asn | Val | Phe | Ser | Cys | Ser |
| | | | 195 | | | | | 200 | | | | | 205 | | |

| Val | Met | His | Glu | Ala | Leu | His | Asn | His | Tyr | Thr | Gln | Lys | Ser | Leu | Ser |
| | 210 | | | | | 215 | | | | | 220 | | | | |

| Leu | Ser | Leu | Gly | Gly | Gly | Gly | Ser | Gly | Gly | Gly | Ser | Gly | Gly |
| 225 | | | | | 230 | | | | | 235 | | | 240 |

| Gly | Gly | Ser | His | Pro | Ile | Pro | Asp | Ser | Ser | Pro | Leu | Leu | Gln | Phe | Gly |
| | | | | 245 | | | | | 250 | | | | | 255 | |

| Gly | Gln | Val | Arg | Gln | Arg | Tyr | Leu | Tyr | Thr | Asp | Asp | Ala | Gln | Gln | Thr |
| | | | | 260 | | | | | 265 | | | | | 270 | |

| Glu | Ala | His | Leu | Glu | Ile | Arg | Glu | Asp | Gly | Thr | Val | Gly | Gly | Ala | Ala |
| | | | 275 | | | | | 280 | | | | | 285 | | |

| Asp | Gln | Ser | Pro | Glu | Ser | Leu | Leu | Gln | Leu | Lys | Ala | Leu | Lys | Pro | Gly |
| | 290 | | | | | 295 | | | | | 300 | | | | |

| Val | Ile | Gln | Ile | Leu | Gly | Val | Lys | Thr | Ser | Arg | Phe | Leu | Cys | Gln | Arg |
| 305 | | | | | 310 | | | | | 315 | | | | | 320 |

| Pro | Asp | Gly | Ala | Leu | Tyr | Gly | Ser | Leu | His | Phe | Asp | Pro | Glu | Ala | Cys |
| | | | | 325 | | | | | 330 | | | | | 335 | |

| Ser | Phe | Arg | Glu | Arg | Leu | Leu | Glu | Asp | Gly | Tyr | Asn | Val | Tyr | Gln | Ser |
| | | | 340 | | | | | 345 | | | | | 350 | | |

| Glu | Ala | His | Arg | Gln | Pro | Leu | His | Leu | Pro | Gly | Asn | Lys | Ser | Pro | His |
| | | | 355 | | | | | 360 | | | | | 365 | | |

| Arg | Asp | Pro | Ala | Pro | Arg | Gly | Pro | Ala | Cys | Phe | Leu | Pro | Leu | Pro | Gly |
| | 370 | | | | | 375 | | | | | 380 | | | | |

| Leu | Pro | Pro | Ala | Leu | Pro | Glu | Pro | Pro | Gly | Ile | Leu | Ala | Pro | Gln | Pro |
| 385 | | | | | 390 | | | | | 395 | | | | | 400 |

| Pro | Asp | Val | Gly | Ser | Ser | Asp | Pro | Leu | His | Met | Val | Gly | Ala | Ser | Gln |
| | | | | 405 | | | | | 410 | | | | | 415 | |

| Gly | Pro | Ser | Pro | Ser | Tyr | Ala | Ser |
| | | | | 420 | | | |

<210> SEQ ID NO 15
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 15

| His | Gly | Glu | Gly | Thr | Phe | Thr | Ser | Asp | Val | Ser | Ser | Tyr | Leu | Glu | Glu |
| 1 | | | | 5 | | | | | 10 | | | | | 15 | |

| Gln | Ala | Ala | Lys | Glu | Phe | Ile | Ala | Trp | Leu | Val | Lys | Gly | Gly | Gly |
| | | | 20 | | | | | 25 | | | | | 30 | |

<210> SEQ ID NO 16
<211> LENGTH: 470
<212> TYPE: PRT
<213> ORGANISM: Artificial Sequence
<220> FEATURE:
<223> OTHER INFORMATION: Fusion Protein D1 98R171A167H

<400> SEQUENCE: 16

-continued

```
His Gly Glu Gly Thr Phe Thr Ser Asp Val Ser Ser Tyr Leu Glu
1               5                   10                  15

Gln Ala Ala Lys Glu Phe Ile Ala Trp Leu Val Lys Gly Gly Gly
                20                  25                  30

Gly Gly Gly Ser Gly Gly Gly Ser Gly Gly Gly Ser Glu Ser
        35                  40                  45

Lys Tyr Gly Pro Pro Cys Pro Pro Cys Pro Ala Pro Glu Ala Ala Gly
    50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95

Glu Asp Pro Glu Val Gln Phe Asn Trp Tyr Val Asp Gly Val Glu Val
                100                 105                 110

His Asn Ala Lys Thr Lys Pro Arg Glu Glu Gln Phe Asn Ser Thr Tyr
                115                 120                 125

Arg Val Val Ser Val Leu Thr Val Leu His Gln Asp Trp Leu Asn Gly
    130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
                180                 185                 190

Leu Thr Cys Leu Val Lys Gly Phe Tyr Pro Ser Asp Ile Ala Val Glu
                195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Glu Gly Asn Val Phe Ser Cys Ser Val Met
                245                 250                 255

His Glu Ala Leu His Asn His Tyr Thr Gln Lys Ser Leu Ser Leu Ser
                260                 265                 270

Leu Gly Gly Gly Gly Ser Gly Gly Gly Ser Gly Gly Gly Gly
    275                 280                 285

Ser His Pro Ile Pro Asp Ser Ser Pro Leu Leu Gln Phe Gly Gly Gln
    290                 295                 300

Val Arg Gln Arg Tyr Leu Tyr Thr Asp Asp Ala Gln Gln Thr Glu Ala
305                 310                 315                 320

His Leu Glu Ile Arg Glu Asp Gly Thr Val Gly Gly Ala Ala Asp Gln
                325                 330                 335

Ser Pro Glu Ser Leu Leu Gln Leu Lys Ala Leu Lys Pro Gly Val Ile
                340                 345                 350

Gln Ile Leu Gly Val Lys Thr Ser Arg Phe Leu Cys Gln Arg Pro Asp
                355                 360                 365

Gly Ala Leu Tyr Gly Ser Leu His Phe Asp Pro Glu Ala Cys Ser Phe
    370                 375                 380

Arg Glu Arg Leu Leu Glu Asp Gly Tyr Asn Val Tyr Gln Ser Glu Ala
385                 390                 395                 400

His Gly Leu Pro Leu His Leu Pro Gly Asn Lys Ser Pro His Arg Asp
                405                 410                 415
```

```
Pro Ala Pro Arg Gly Pro Ala Arg Phe Leu Pro Leu Pro Gly Leu Pro
            420                 425                 430

Pro Ala Leu Pro Glu Pro Gly Ile Leu Ala Pro Gln Pro Pro Asp
        435                 440                 445

Val Gly Ser Ser Asp Pro Leu His Met Val Gly Ala Ser Gln Gly Arg
    450                 455                 460

Ser Pro Ser Tyr Ala Ser
465                 470

<210> SEQ ID NO 17
<211> LENGTH: 470
<212> TYPE: PRT
<213> ORGANISM: Artificial Sequence
<220> FEATURE:
<223> OTHER INFORMATION: Fusion Protein D2 98R171A167H175L

<400> SEQUENCE: 17

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Glu Ser
        35                  40                  45

Lys Tyr Gly Pro Pro Cys Pro Pro Cys Pro Ala Pro Glu Ala Ala Gly
50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
            85                  90                  95

Glu Asp Pro Glu Val Gln Phe Asn Trp Tyr Val Asp Gly Val Glu Val
        100                 105                 110

His Asn Ala Lys Thr Lys Pro Arg Glu Glu Gln Phe Asn Ser Thr Tyr
    115                 120                 125

Arg Val Val Ser Val Leu Thr Val Leu His Gln Asp Trp Leu Asn Gly
130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
            165                 170                 175

Tyr Thr Leu Pro Pro Ser Gln Glu Glu Met Thr Lys Asn Gln Val Ser
        180                 185                 190

Leu Thr Cys Leu Val Lys Gly Phe Tyr Pro Ser Asp Ile Ala Val Glu
    195                 200                 205

Trp Glu Ser Asn Gly Gln Pro Glu Asn Asn Tyr Lys Thr Thr Pro Pro
210                 215                 220

Val Leu Asp Ser Asp Gly Ser Phe Phe Leu Tyr Ser Lys Leu Thr Val
225                 230                 235                 240

Asp Lys Ser Arg Trp Gln Glu Gly Asn Val Phe Ser Cys Ser Val Met
            245                 250                 255

His Glu Ala Leu His Asn His Tyr Thr Gln Lys Ser Leu Ser Leu Ser
        260                 265                 270

Leu Gly Gly Gly Gly Ser Gly Gly Gly Ser Gly Gly Gly Gly
    275                 280                 285

Ser His Pro Ile Pro Asp Ser Ser Pro Leu Leu Gln Phe Gly Gly Gln
290                 295                 300
```

```
Val Arg Gln Arg Tyr Leu Tyr Thr Asp Asp Ala Gln Gln Thr Glu Ala
305                 310                 315                 320

His Leu Glu Ile Arg Glu Asp Gly Thr Val Gly Gly Ala Ala Asp Gln
            325                 330                 335

Ser Pro Glu Ser Leu Leu Gln Leu Lys Ala Leu Lys Pro Gly Val Ile
        340                 345                 350

Gln Ile Leu Gly Val Lys Thr Ser Arg Phe Leu Cys Gln Arg Pro Asp
            355                 360                 365

Gly Ala Leu Tyr Gly Ser Leu His Phe Asp Pro Glu Ala Cys Ser Phe
        370                 375                 380

Arg Glu Arg Leu Leu Glu Asp Gly Tyr Asn Val Tyr Gln Ser Glu Ala
385                 390                 395                 400

His Gly Leu Pro Leu His Leu Pro Gly Asn Lys Ser Pro His Arg Asp
            405                 410                 415

Pro Ala Pro Arg Gly Pro Ala Arg Phe Leu Pro Leu Pro Gly Leu Pro
        420                 425                 430

Pro Ala Leu Pro Glu Pro Gly Ile Leu Ala Pro Gln Pro Pro Asp
        435                 440                 445

Val Gly Ser Ser Asp Pro Leu His Met Val Gly Ala Ser Gln Gly Leu
450                 455                 460

Ser Pro Ser Tyr Ala Ser
465             470

<210> SEQ ID NO 18
<211> LENGTH: 470
<212> TYPE: PRT
<213> ORGANISM: Artificial Sequence
<220> FEATURE:
<223> OTHER INFORMATION: Fusion Protein D3 98R171G167H175L

<400> SEQUENCE: 18

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Gly Ser Gly Gly Gly Gly Ser Glu Ser
        35                  40                  45

Lys Tyr Gly Pro Pro Cys Pro Pro Cys Pro Ala Pro Glu Ala Ala Gly
50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
            85                  90                  95

Glu Asp Pro Glu Val Gln Phe Asn Trp Tyr Val Asp Gly Val Glu Val
        100                 105                 110

His Asn Ala Lys Thr Lys Pro Arg Glu Glu Gln Phe Asn Ser Thr Tyr
    115                 120                 125

Arg Val Val Ser Val Leu Thr Val Leu His Gln Asp Trp Leu Asn Gly
130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
            165                 170                 175

Tyr Thr Leu Pro Pro Ser Gln Glu Glu Met Thr Lys Asn Gln Val Ser
        180                 185                 190
```

-continued

```
Leu Thr Cys Leu Val Lys Gly Phe Tyr Pro Ser Asp Ile Ala Val Glu
            195                 200                 205

Trp Glu Ser Asn Gly Gln Pro Glu Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Gly Asn Val Phe Ser Cys Ser Val Met
                245                 250                 255

His Glu Ala Leu His Asn His Tyr Thr Gln Lys Ser Leu Ser Leu Ser
            260                 265                 270

Leu Gly Gly Gly Gly Ser Gly Gly Gly Gly Ser Gly Gly Gly Gly
            275                 280                 285

Ser His Pro Ile Pro Asp Ser Ser Pro Leu Leu Gln Phe Gly Gly Gln
    290                 295                 300

Val Arg Gln Arg Tyr Leu Tyr Thr Asp Asp Ala Gln Gln Thr Glu Ala
305                 310                 315                 320

His Leu Glu Ile Arg Glu Asp Gly Thr Val Gly Gly Ala Ala Asp Gln
                325                 330                 335

Ser Pro Glu Ser Leu Leu Gln Leu Lys Ala Leu Lys Pro Gly Val Ile
            340                 345                 350

Gln Ile Leu Gly Val Lys Thr Ser Arg Phe Leu Cys Gln Arg Pro Asp
            355                 360                 365

Gly Ala Leu Tyr Gly Ser Leu His Phe Asp Pro Glu Ala Cys Ser Phe
    370                 375                 380

Arg Glu Arg Leu Leu Glu Asp Gly Tyr Asn Val Tyr Gln Ser Glu Ala
385                 390                 395                 400

His Gly Leu Pro Leu His Leu Pro Gly Asn Lys Ser Pro His Arg Asp
                405                 410                 415

Pro Ala Pro Arg Gly Pro Ala Arg Phe Leu Pro Leu Pro Gly Leu Pro
            420                 425                 430

Pro Ala Leu Pro Glu Pro Pro Gly Ile Leu Ala Pro Gln Pro Pro Asp
            435                 440                 445

Val Gly Ser Ser Asp Pro Leu His Met Val Gly Gly Ser Gln Gly Leu
    450                 455                 460

Ser Pro Ser Tyr Ala Ser
465                 470

<210> SEQ ID NO 19
<211> LENGTH: 1272
<212> TYPE: DNA
<213> ORGANISM: Artificial Sequence
<220> FEATURE:
<223> OTHER INFORMATION: DNA Encoding Fusion Protein S1 98R171A167H

<400> SEQUENCE: 19
gagagcaagt acggccccccc ctgtcctcct tgccccgccc ctgaggccgc cggcggccct      60
agcgtgtttc tgtttccccc caagcctaaa gacaccctga tgatctccag gacccctgag     120
gtgacctgtg tggtggtgga cgtgagccag gaggaccccg aggtgcagtt caactggtac     180
gtggatggcg tggaagtgca caacgccaag accaagccca gggaggagca attcaacagc     240
acctacaggg tggtgagcgt cctcaccgtc ctgcatcagg actggctgaa cggcaaggag     300
tacaagtgca agtgtccaa caagggcctg ccttcctcca tcgagaagac catctccaag     360
gctaagggcc agcccaggga accccaagtg tacaccctcc cccctcccca ggaggagatg     420 accaaaaaacc aagtctccct gacctgcctg gtgaagggct tctaccctc cgatattgcc     480
```

```
gtcgagtggg agagcaacgg ccagcccgag aacaactata agaccacccc ccccgtgctg      540
gattccgacg gttctttttt cctgtatagc aagctgaccg tggacaagtc caggtggcag      600
gagggcaacg tgttctcctg cagcgtgatg cacgaggccc tccacaacca ctacacccag      660
aaatccctgt ccctgtccct cggcggcgga ggcggctccg gcggcggcgg cagcggaggc      720
ggaggaagcc atcccattcc cgactccagc cccctgctgc agtttggcgg ccaagtgagg      780
cagagatacc tgtacaccga cgatgcccaa cagacagagg ctcacctgga aatcagggag      840
gacggcaccg tgggcggagc tgctgatcag agccccgagt ccctcctcca gctgaaggcc      900
ctgaagcccg gagtgatcca gatcctgggc gtgaagacat ccaggttcct gtgccagaga      960
cccgatggcg ccctgtacgg aagcctgcac ttcgaccccg aggcttgctc cttcagggag     1020
aggctgctgg aggacggcta caacgtgtac cagtccgagg ctcacggact ccctctgcac     1080
ctgcctggca acaagagccc tcacagagac cccgccccta gaggccctgc taggtttctg     1140
cccctgcctg gcctgcctcc tgctctgccc gagccccctg gtattttagc tcctcagcct     1200
cccgatgtgg aagcagcga ccccctgcac atggtgggag ctagccaggg caggagccct     1260
agctacgcca gc                                                         1272
```

<210> SEQ ID NO 20
<211> LENGTH: 1272
<212> TYPE: DNA
<213> ORGANISM: Artificial Sequence
<220> FEATURE:
<223> OTHER INFORMATION: DNA Encoding Fusion Protein S2 98R171A167H175L

<400> SEQUENCE: 20

```
gagagcaagt acggcccccc ctgtcctcct tgccccgccc ctgaggccgc cggcggccct       60
agcgtgtttc tgtttccccc caagcctaaa gacaccctga tgatctccag gaccccgag      120 gtgacctgtg tggtggtgga cgtgagccag gaggaccccg aggtgcagtt caactggtac      180
gtggatggcg tggaagtgca caacgccaag accaagccca gggaggagca attcaacagc      240
acctacaggg tggtgagcgt cctcaccgtc ctgcatcagg actggctgaa cggcaaggag      300
tacaagtgca aagtgtccaa caagggcctg ccttcctcca tcgagaagac catctccaag      360
gctaagggcc agcccaggga accccaagtg tacaccctcc cccccctccca ggaggagatg      420 accaaaaaac cagtctcccct gacctgcctg gtgaagggct tctaccccct cgatattgcc      480
gtcgagtggg agagcaacgg ccagcccgag aacaactata agaccacccc ccccgtgctg      540
gattccgacg gttctttttt cctgtatagc aagctgaccg tggacaagtc caggtggcag      600
gagggcaacg tgttctcctg cagcgtgatg cacgaggccc tccacaacca ctacacccag      660
aaatccctgt ccctgtccct cggcggcgga ggcggctccg gcggcggcgg cagcggaggc      720
ggaggaagcc atcccattcc cgactccagc cccctgctgc agtttggcgg ccaagtgagg      780
cagagatacc tgtacaccga cgatgcccaa cagacagagg ctcacctgga aatcagggag      840
gacggcaccg tgggcggagc tgctgatcag agccccgagt ccctcctcca gctgaaggcc      900
ctgaagcccg gagtgatcca gatcctgggc gtgaagacat ccaggttcct gtgccagaga      960
cccgatggcg ccctgtacgg aagcctgcac ttcgaccccg aggcttgctc cttcagggag     1020
aggctgctgg aggacggcta caacgtgtac cagtccgagg ctcacggact ccctctgcac     1080
ctgcctggca acaagagccc tcacagagac cccgccccta gaggccctgc taggtttctg     1140
cccctgcctg gcctgcctcc tgctctgccc gagccccctg gtattttagc tcctcagcct     1200
```

```
cccgatgtgg gaagcagcga ccccctgcac atggtgggag ctagccaggg cctgagccct      1260
agctacgcca gc                                                           1272
```

<210> SEQ ID NO 21
<211> LENGTH: 1272
<212> TYPE: DNA
<213> ORGANISM: Artificial Sequence
<220> FEATURE:
<223> OTHER INFORMATION: DNA Encoding Fusion Protein S4 98R171A167H175P

<400> SEQUENCE: 21

```
gagagcaagt acggcccccc ctgtcctcct tgccccgccc ctgaggccgc cggcggccct        60
agcgtgtttc tgtttccccc caagcctaaa gacaccctga tgatctccag gacccctgag      120
gtgacctgtg tggtggtgga cgtgagccag gaggaccccg aggtgcagtt caactggtac      180
gtggatggcg tggaagtgca caacgccaag accaagccca gggaggagca attcaacagc      240
acctacaggg tggtgagcgt cctcaccgtc ctgcatcagg actggctgaa cggcaaggag      300
tacaagtgca aagtgtccaa caagggcctg ccttcctcca tcgagaagac catctccaag      360
gctaagggcc agcccaggga accccaagtg tacaccctcc cccccctccca ggaggagatg      420 accaaaaacc aagtctccct gacctgcctg gtgaagggct tctaccccctc cgatattgcc      480 gtcgagtggg agagcaacgg ccagcccgag aacaactata agaccacccc ccccgtgctg      540
gattccgacg gttcttttttt cctgtatagc aagctgaccg tggacaagtc caggtggcag      600
gagggcaacg tgttctcctg cagcgtgatg cacgaggccc tccacaacca ctacacccag      660
aaatccctgt ccctgtccct cggcggcgga ggcggctccg gcggcggcgg cagcggaggc      720
ggaggaagcc atcccattcc cgactccagc ccctgctgc agtttggcgg ccaagtgagg      780
cagagatacc tgtacaccga cgatgccaa cagacagagg ctcacctgga aatcaggag      840 gacggcaccg tgggcggagc tgctgatcag agccccgagt ccctcctcca gctgaaggcc      900
ctgaagcccg agtgatcca gatcctgggc gtgaagacat ccaggttcct gtgccagaga      960
cccgatggcg ccctgtacgg aagcctgcac ttcgaccccg aggcttgctc cttcagggag     1020
aggctgctgg aggacggcta caacgtgtac cagtccgagg ctcacggact ccctctgcac     1080
ctgcctggca acaagagccc tcacagagac cccgcccta gaggccctgc taggtttctg     1140 ccctgcctg gcctgcctcc tgctctgccc gagccccctg gtattttagc tcctcagcct     1200
cccgatgtgg aagcagcga ccccctgcac atggtgggag ctagccaggg cctagccct     1260 agctacgcca gc                                                           1272
```

<210> SEQ ID NO 22
<211> LENGTH: 1272
<212> TYPE: DNA
<213> ORGANISM: Artificial Sequence
<220> FEATURE:
<223> OTHER INFORMATION: DNA Encoding Fusion Protein S5 98R171A167H175H

<400> SEQUENCE: 22

```
gagagcaagt acggcccccc ctgtcctcct tgccccgccc ctgaggccgc cggcggccct        60
agcgtgtttc tgtttccccc caagcctaaa gacaccctga tgatctccag gacccctgag      120
gtgacctgtg tggtggtgga cgtgagccag gaggaccccg aggtgcagtt caactggtac      180
gtggatggcg tggaagtgca caacgccaag accaagccca gggaggagca attcaacagc      240
acctacaggg tggtgagcgt cctcaccgtc ctgcatcagg actggctgaa cggcaaggag      300
tacaagtgca aagtgtccaa caagggcctg ccttcctcca tcgagaagac catctccaag      360
```

```
gctaagggcc agcccaggga accccaagtg tacaccctcc cccctccca ggaggagatg        420
accaaaaacc aagtctccct gacctgcctg gtgaagggct tctacccctc cgatattgcc        480
gtcgagtggg agagcaacgg ccagcccgag aacaactata agaccacccc ccccgtgctg        540
gattccgacg gttctttttt cctgtatagc aagctgaccg tggacaagtc caggtggcag        600
gagggcaacg tgttctcctg cagcgtgatg cacgaggccc tccacaacca ctacacccag        660
aaatccctgt ccctgtccct cggcggcgga ggcggctccg gcggcggcgg cagcggaggc        720
ggaggaagcc atcccattcc cgactccagc cccctgctgc agtttggcgg ccaagtgagg        780
cagagatacc tgtacaccga cgatgccaa cagacagagg ctcacctgga aatcagggag        840
gacggcaccg tgggcggagc tgctgatcag agccccgagt ccctcctcca gctgaaggcc        900
ctgaagcccg gagtgatcca gatcctgggc gtgaagacat ccaggttcct gtgccagaga        960
cccgatggcg ccctgtacgg aagcctgcac ttcgaccccg aggcttgctc cttcagggag       1020
aggctgctgg aggacggcta caacgtgtac cagtccgagg ctcacggact ccctctgcac       1080
ctgcctggca caagagccc tcacagagac cccgcccta gaggccctgc taggtttctg       1140
cccctgcctg gcctgcctcc tgctctgccc gagccccctg gtattttagc tcctcagcct       1200
cccgatgtgg aagcagcga ccccctgcac atggtgggag ctagccaggg ccacagccct       1260
agctacgcca gc                                                           1272

<210> SEQ ID NO 23
<211> LENGTH: 1272
<212> TYPE: DNA
<213> ORGANISM: Artificial Sequence
<220> FEATURE:
<223> OTHER INFORMATION: DNA Encoding Fusion Protein S6
      98R171A167H175P113R114Q135C

<400> SEQUENCE: 23
gagagcaagt atggccccc ttgtcctccc tgtcccgctc ctgaggccgc cggcggcccc         60
agcgtgtttc tgtttccccc caagcccaaa gacacactga tgatcagcag gacacccgaa        120
gtgacctgcg tggtcgtgga cgtgtcccag gaagaccccg aggtgcagtt taactggtac        180
gtcgacggag tcgaggtgca caacgccaag accaagccca gagaggagca gttcaacagc        240
acctacagag tggtgagcgt gctgaccgtg ctgcatcagg actggctgaa cggcaaggag        300
tacaagtgca aggtcagcaa caagggcctg cctagcagca tcgagaagac catctccaag        360
gccaagggcc aacccaggga accccaagtg tacaccctgc ctcccagcca ggaggagatg        420
accaagaacc aggtgtccct gacctgcctc gtcaagggct tttacccttc cgacatcgcc        480
gtggagtggg aatccaacgg ccagcccgag aataactaca aaaccacccc ccccgtgctc        540
gatagcgatg gctccttctt cctctacagc aagctgacag tcgataagtc caggtggcag        600
gagggaaacg tcttctcctg cagcgtgatg cacgaggctc tccacaacca ctacacccag        660
aagtccctga gcctgagcct gggcggcgg ggcggcagcg gcggcggagg cagcggcggc        720
ggcggaagcc atcccatccc tgatagcagc cctctgctcc agttcggcgg ccaagtgagg        780
cagagatacc tgtacaccga cgatgccag cagacagaag cccacctgga gatcagagag        840
gacggaacag tgggcggagc tgccgaccag tcccccgaat ccctgctgca gctgaaggcc        900
ctgaagcccg gagtgatcca gatcctgggc gtcaagacct ccaggttcct gtgccagagg        960
cccgatggcg ctctgtatgg cagcctgcac tttgaccccg aggcctgttc cttcagggag       1020
agactcctgg aggatggcta caacgtctac cagtccgaag cccacagaca gcccctgcac       1080
```

```
ctgcccggca acaaatcccc tcacagggat cctgctccca gaggccctgc ttgcttcctg    1140
cctctccctg gactgcctcc tgccctcccc gaacctcctg gcattctggc ccctcagcct    1200
cctgatgtgg gcagcagcga ccctctgcac atggtgggag ccagccaagg acccagcccc    1260
tcctacgcca gc                                                        1272
```

<210> SEQ ID NO 24
<211> LENGTH: 1410
<212> TYPE: DNA
<213> ORGANISM: Artificial Sequence
<220> FEATURE:
<223> OTHER INFORMATION: DNA Encoding Fusion Protein D1 98R171A167H

<400> SEQUENCE: 24

```
catggcgagg gcacctttac ctccgacgtg tcctcctacc tggaagaaca ggccgccaaa      60
gagtttatcg cctggctcgt gaagggcggt ggtggcggcg gaggatctgg cggaggtgga    120
agcggaggcg gtggatctga gagcaagtac ggcccccccct gtcctccttg ccccgccccct   180 gaggccgccg gcggccctag cgtgtttctg tttccccccca agcctaaaga caccctgatg   240
atctccagga ccccctgaggt gacctgtgtg gtggtggacg tgagccagga ggaccccgag   300
gtgcagttca actggtacgt ggatggcgtg gaagtgcaca acgccaagac caagcccagg   360
gaggagcaat tcaacagcac ctacagggtg gtgagcgtcc tcaccgtcct gcatcaggac   420
tggctgaacg gcaaggagta caagtgcaaa gtgtccaaca agggcctgcc ttcctccatc   480
gagaagacca tctccaaggc taagggccag cccaggaac cccaagtgta cacccctccc    540
ccctcccagg aggagatgac caaaaaccaa gtctccctga cctgcctggt gaagggcttc   600 taccccctccg atattgccgt cgagtgggag agcaacggcc agcccgagaa caactataag   660
accacccccc ccgtgctgga ttccgacggt tcttttttcc tgtatagcaa gctgaccgtg   720
gacaagtcca ggtggcagga gggcaacgtg ttctcctgca gcgtgatgca cgaggccctc   780
cacaaccact acacccagaa atccctgtcc ctgtccctcg gcggcggagg cggctccggc   840
ggcggcggca gcggaggcgg aggaagccat cccattcccg actccagccc cctgctgcag   900
tttggcggcc aagtgaggca gagatacctg tacaccgacg atgcccaaca dacagaggct   960
cacctggaaa tcagggagga cggcaccgtg ggcggagctg ctgatcagag ccccgagtcc  1020
ctcctccagc tgaaggccct gaagcccgga gtgatccaga tcctgggcgt gaagacatcc  1080
aggttcctgt gccagagacc cgatggcgcc ctgtacggaa gcctgcactt cgaccccgag  1140
gcttgctcct tcagggagag gctgctggag gacggctaca acgtgtacca gtccgaggct  1200
cacggactcc ctctgcacct gcctggcaac aagagccctc acagagaccc gcccctaga   1260 ggccctgcta ggtttctgcc cctgcctggc ctgcctcctg ctctgcccga gccccctggt  1320
attttagctc ctcagcctcc cgatgtggga agcagcgacc ccctgcacat ggtgggagct  1380
agccagggca ggagccctag ctacgccagc                                    1410
```

<210> SEQ ID NO 25
<211> LENGTH: 1410
<212> TYPE: DNA
<213> ORGANISM: Artificial Sequence
<220> FEATURE:
<223> OTHER INFORMATION: DNA Encoding Fusion Protein D2 98R171A167H175L

<400> SEQUENCE: 25

```
catggcgagg gcacctttac ctccgacgtg tcctcctacc tggaagaaca ggccgccaaa     60
```

```
gagtttatcg cctggctcgt gaagggcggt ggtggcggcg gaggatctgg cggaggtgga    120
agcggaggcg gtggatctga gagcaagtac ggcccccct gtcctccttg ccccgccct     180
gaggccgccg gcggccctag cgtgtttctg tttccccca agcctaaaga caccctgatg    240
atctccagga cccctgaggt gacctgtgtg gtggtggacg tgagccagga ggaccccgag   300
gtgcagttca actggtacgt ggatggcgtg gaagtgcaca acgccaagac caagcccagg   360
gaggagcaat tcaacagcac ctacagggtg gtgagcgtcc tcaccgtcct gcatcaggac   420
tggctgaacg gcaaggagta caagtgcaaa gtgtccaaca agggcctgcc ttcctccatc   480
gagaagacca tctccaaggc taagggccag cccagggaac ccaagtgta caccctcccc    540
ccctcccagg aggagatgac caaaaaccaa gtctccctga cctgcctggt gaagggcttc   600
taccctccg atattgccgt cgagtgggag agcaacggcc agcccgagaa caactataag    660
accacccccc ccgtgctgga ttccgacggt tctttttttc tgtatagcaa gctgaccgtg   720
gacaagtcca gtggcagga gggcaacgtg ttctcctgca gcgtgatgca cgaggccctc    780
cacaaccact acacccagaa atccctgtcc ctgtccctcg gcggcggagg cggctccggc   840
ggcggcggca gcggaggcgg aggaagccat cccattcccg actccagccc cctgctgcag   900
tttggcggcc aagtgaggca gagataccg tacaccgacg atgcccaaca gacagaggct    960
cacctggaaa tcagggagga cggcaccgtg ggcggagctg ctgatcagag ccccgagtcc   1020
ctcctccagc tgaaggccct gaagcccgga gtgatccaga tcctgggcgt gaagacatcc   1080
aggttcctgt gccagagacc cgatggcgcc ctgtacggaa gcctgcactt cgaccccgag   1140
gcttgctcct tcagggagag gctgctggag gacggctaca acgtgtacca gtccgaggct   1200
cacggactcc ctctgcacct gcctggcaac aagagccctc acagagaccc cgcccctaga   1260
ggccctgcta ggtttctgcc cctgcctggc ctgcctcctg ctctgccga gccccctggt   1320
attttagctc ctcagcctcc cgatgtggga agcagcgacc ccctgcacat ggtgggagct   1380
agccagggcc tgagccctag ctacgccagc                                    1410
```

```
<210> SEQ ID NO 26
<211> LENGTH: 424
<212> TYPE: PRT
<213> ORGANISM: Artificial Sequence
<220> FEATURE:
<223> OTHER INFORMATION: Fusion Protein S7 98R171A

<400> SEQUENCE: 26
```

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

```
Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Gly Gly Gly Ser Gly Gly Gly Ser Gly Gly
225                 230                 235                 240

Gly Gly Ser His Pro Ile Pro Asp Ser Ser Pro Leu Leu Gln Phe Gly
                245                 250                 255

Gly Gln Val Arg Gln Arg Tyr Leu Tyr Thr Asp Asp Ala Gln Gln Thr
            260                 265                 270

Glu Ala His Leu Glu Ile Arg Glu Asp Gly Thr Val Gly Gly Ala Ala
            275                 280                 285

Asp Gln Ser Pro Glu Ser Leu Leu Gln Leu Lys Ala Leu Lys Pro Gly
290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Arg Leu Leu Glu Asp Gly Tyr Asn Val Tyr Gln Ser
            340                 345                 350

Glu Ala His Gly Leu Pro Leu His Leu Pro Gly Asn Lys Ser Pro His
            355                 360                 365

Arg Asp Pro Ala Pro Arg Gly Pro Ala Arg Phe Leu Pro Leu Pro Gly
370                 375                 380

Leu Pro Pro Ala Leu Pro Glu Pro Pro Gly Ile Leu Ala Pro Gln Pro
385                 390                 395                 400

Pro Asp Val Gly Ser Ser Asp Pro Leu Ser Met Val Gly Ala Ser Gln
                405                 410                 415

Gly Arg Ser Pro Ser Tyr Ala Ser
                420

<210> SEQ ID NO 27
<211> LENGTH: 424
<212> TYPE: PRT
<213> ORGANISM: Artificial Sequence
<220> FEATURE:
<223> OTHER INFORMATION: Fusion Protein S8 98R171G

<400> SEQUENCE: 27

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
50                  55                  60
```

-continued

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
            85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Gly Gly Gly Ser Gly Gly Gly Ser Gly Gly
225                 230                 235                 240

Gly Gly Ser His Pro Ile Pro Asp Ser Ser Pro Leu Leu Gln Phe Gly
            245                 250                 255

Gly Gln Val Arg Gln Arg Tyr Leu Tyr Thr Asp Asp Ala Gln Gln Thr
            260                 265                 270

Glu Ala His Leu Glu Ile Arg Glu Asp Gly Thr Val Gly Gly Ala Ala
        275                 280                 285

Asp Gln Ser Pro Glu Ser Leu Leu Gln Leu Lys Ala Leu Lys Pro Gly
290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
            325                 330                 335

Ser Phe Arg Glu Arg Leu Leu Glu Asp Gly Tyr Asn Val Tyr Gln Ser
            340                 345                 350

Glu Ala His Gly Leu Pro Leu His Leu Pro Gly Asn Lys Ser Pro His
        355                 360                 365

Arg Asp Pro Ala Pro Arg Gly Pro Ala Arg Phe Leu Pro Leu Pro Gly
370                 375                 380

Leu Pro Pro Ala Leu Pro Glu Pro Pro Gly Ile Leu Ala Pro Gln Pro
385                 390                 395                 400

Pro Asp Val Gly Ser Ser Asp Pro Leu Ser Met Val Gly Gly Ser Gln
            405                 410                 415

Gly Arg Ser Pro Ser Tyr Ala Ser
            420

<210> SEQ ID NO 28
<211> LENGTH: 31
<212> TYPE: PRT
<213> ORGANISM: Artificial Sequence
<220> FEATURE:
<223> OTHER INFORMATION: GLP-1 analogue

<400> SEQUENCE: 28

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly
            20                  25                  30

<210> SEQ ID NO 29
<211> LENGTH: 37
<212> TYPE: DNA
<213> ORGANISM: Artificial Sequence
<220> FEATURE:
<223> OTHER INFORMATION: Primer AUZ-F

<400> SEQUENCE: 29
cccaagcttg ccgccaccat gaccagactg accgtgc                                37

<210> SEQ ID NO 30
<211> LENGTH: 35
<212> TYPE: DNA
<213> ORGANISM: Artificial Sequence
<220> FEATURE:
<223> OTHER INFORMATION: Primer lfc1-R

<400> SEQUENCE: 30
gccgtacttg ctctcagatc caccgcctcc gcttc                                  35

<210> SEQ ID NO 31
<211> LENGTH: 34
<212> TYPE: DNA
<213> ORGANISM: Artificial Sequence
<220> FEATURE:
<223> OTHER INFORMATION: Primer lfc1-F

<400> SEQUENCE: 31
gcggaggcgg tggatctgag agcaagtacg gccc                                   34

<210> SEQ ID NO 32
<211> LENGTH: 33
<212> TYPE: DNA
<213> ORGANISM: Artificial Sequence
<220> FEATURE:
<223> OTHER INFORMATION: Primer fgf21-R

<400> SEQUENCE: 32
ccggaattct catcagctgg cgtagctagg gct                                    33

<210> SEQ ID NO 33
<211> LENGTH: 192
<212> TYPE: PRT
<213> ORGANISM: Artificial Sequence
<220> FEATURE:
<223> OTHER INFORMATION: Control fusion protein SPC

<400> SEQUENCE: 33

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

```
Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190
```

<210> SEQ ID NO 34
<211> LENGTH: 181
<212> TYPE: PRT
<213> ORGANISM: Artificial Sequence
<220> FEATURE:
<223> OTHER INFORMATION: Sequence of FGF21 variant in S1

<400> SEQUENCE: 34

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Arg Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu His Met Val Gly Ala Ser Gln Gly Arg Ser
                165                 170                 175

Pro Ser Tyr Ala Ser
            180
```

<210> SEQ ID NO 35
<211> LENGTH: 181
<212> TYPE: PRT
<213> ORGANISM: Artificial Sequence
<220> FEATURE:
<223> OTHER INFORMATION: Sequence of FGF21 variant in S4

<400> SEQUENCE: 35

His Pro Ile Pro Asp Ser Ser Pro Leu Leu Gln Phe Gly Gly Gln Val

```
                1               5                   10                  15
            Arg Gln Arg Tyr Leu Tyr Thr Asp Asp Ala Gln Gln Thr Glu Ala His
                            20                  25                  30

Leu Glu Ile Arg Glu Asp Gly Thr Val Gly Gly Ala Ala Asp Gln Ser
                        35                  40                  45

Pro Glu Ser Leu Leu Gln Leu Lys Ala Leu Lys Pro Gly Val Ile Gln
                50                  55                  60

Ile Leu Gly Val Lys Thr Ser Arg Phe Leu Cys Gln Arg Pro Asp Gly
            65                  70                  75                  80

Ala Leu Tyr Gly Ser Leu His Phe Asp Pro Glu Ala Cys Ser Phe Arg
                            85                  90                  95

Glu Arg Leu Leu Glu Asp Gly Tyr Asn Val Tyr Gln Ser Glu Ala His
                        100                 105                 110

Gly Leu Pro Leu His Leu Pro Gly Asn Lys Ser Pro His Arg Asp Pro
                        115                 120                 125

Ala Pro Arg Gly Pro Ala Arg Phe Leu Pro Leu Pro Gly Leu Pro Pro
                        130                 135                 140

Ala Leu Pro Glu Pro Pro Gly Ile Leu Ala Pro Gln Pro Pro Asp Val
            145                 150                 155                 160

Gly Ser Ser Asp Pro Leu His Met Val Gly Ala Ser Gln Gly Pro Ser
                            165                 170                 175

Pro Ser Tyr Ala Ser
                        180

<210> SEQ ID NO 36
            <211> LENGTH: 181
            <212> TYPE: PRT
            <213> ORGANISM: Artificial Sequence
            <220> FEATURE:
            <223> OTHER INFORMATION: Sequence of FGF21 variant in S5

<400> SEQUENCE: 36

His Pro Ile Pro Asp Ser Ser Pro Leu Leu Gln Phe Gly Gly Gln Val
            1               5                   10                  15

Arg Gln Arg Tyr Leu Tyr Thr Asp Asp Ala Gln Gln Thr Glu Ala His
                            20                  25                  30

Leu Glu Ile Arg Glu Asp Gly Thr Val Gly Gly Ala Ala Asp Gln Ser
                        35                  40                  45

Pro Glu Ser Leu Leu Gln Leu Lys Ala Leu Lys Pro Gly Val Ile Gln
                50                  55                  60

Ile Leu Gly Val Lys Thr Ser Arg Phe Leu Cys Gln Arg Pro Asp Gly
            65                  70                  75                  80

Ala Leu Tyr Gly Ser Leu His Phe Asp Pro Glu Ala Cys Ser Phe Arg
                            85                  90                  95

Glu Arg Leu Leu Glu Asp Gly Tyr Asn Val Tyr Gln Ser Glu Ala His
                        100                 105                 110

Gly Leu Pro Leu His Leu Pro Gly Asn Lys Ser Pro His Arg Asp Pro
                        115                 120                 125

Ala Pro Arg Gly Pro Ala Arg Phe Leu Pro Leu Pro Gly Leu Pro Pro
                        130                 135                 140

Ala Leu Pro Glu Pro Pro Gly Ile Leu Ala Pro Gln Pro Pro Asp Val
            145                 150                 155                 160

Gly Ser Ser Asp Pro Leu His Met Val Gly Ala Ser Gln Gly His Ser
                            165                 170                 175

Pro Ser Tyr Ala Ser
```

```
            180

<210> SEQ ID NO 37
<211> LENGTH: 181
<212> TYPE: PRT
<213> ORGANISM: Artificial Sequence
<220> FEATURE:
<223> OTHER INFORMATION: Sequence of FGF21 variant in S6

<400> SEQUENCE: 37

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
            85                  90                  95

Glu Arg Leu Leu Glu Asp Gly Tyr Asn Val Tyr Gln Ser Glu Ala His
            100                 105                 110

Gln Gln Pro Leu His Leu Pro Gly Asn Lys Ser Pro His Arg Asp Pro
        115                 120                 125

Ala Pro Arg Gly Pro Ala Cys Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu His Met Val Gly Ala Ser Gln Gly Pro Ser
                165                 170                 175

Pro Ser Tyr Ala Ser
                180
```